United States Patent [19]

McCarthy et al.

[11] Patent Number: 5,952,176
[45] Date of Patent: Sep. 14, 1999

[54] GLYCOSYLASE MEDIATED DETECTION OF NUCLEOTIDE SEQUENCES AT CANDIDATE LOCI

[75] Inventors: Thomas Valentine McCarthy, Montenotte; Patrick Martin Vaughan, Frankfield, both of Ireland

[73] Assignee: FORFAS (Trading as Bioresearch Ireland), Dublin, Ireland

[21] Appl. No.: 08/981,663

[22] PCT Filed: Dec. 21, 1995

[86] PCT No.: PCT/IE95/00067

§ 371 Date: Jan. 8, 1998

§ 102(e) Date: Jan. 8, 1998

[87] PCT Pub. No.: WO97/03210

PCT Pub. Date: Jan. 30, 1997

[30] Foreign Application Priority Data

Jul. 11, 1996 [IE] Ireland ..................... 950526

[51] Int. Cl.⁶ .................. C12Q 1/68; C12P 19/34
[52] U.S. Cl. ............................ 435/6; 435/91.2
[58] Field of Search .......................... 435/6, 91.2

[56] References Cited

PUBLICATIONS

Sanger et al., J. Mol. Biol. (1975) 94, 441–448.
Maxam et al., Proc. Natl. Acad. Sci. USA, vol. 74, No. 2, pp. 560–564, Feb. 1977.

*Primary Examiner*—Eggerton A. Campbell
*Attorney, Agent, or Firm*—Birch, Stewart, Kolasch & Birch, LLP

[57] ABSTRACT

A novel process is presented for the detection of known mutations and polymorphisms in DNA. This process, termed glycosylase mediated polymorphism detection (GMPD) involves amplification of the target DNA using three normal dNTPs and a fourth modified dNTP, whose base is a substrate for a specific DNA-glycosylase once incorporated into the DNA.

20 Claims, 14 Drawing Sheets normal allele

PCR amplification using
dGTP, dATP, dCTP and dUTP

5' gccccctgagatcaagtacGgggagucacugugcuucgug 3'

3' cgggggacucuaguucaugCccctcagtgacacgaagcac 5' *

Removal of primers not utilised
in amplification and incubation
with Uracil-DNA-Glycosylase (- = AP site)

5' gccccctgagatcaagtacGgggag-cac-g-gc--cg-g 3'

3' cgggggac-c-ag--ca-gCccctcagtgacacgaagcac 5' *

Cleavage of AP sites by treatment
with alkali and heat

5' gccccctgagatcaagtacGgggag cac g gc  cg g 3'

3' cgggggac c ag  ca gCccctcagtgacacgaagcac 5' * labelled 22 nucleotide
fragment

Denaturing polyacrylamide gel
electrophoresis and autoradiography

FIG. 1A mutant allele

5′ distal primer 3′
gccccctgagatcaagtac
5′ gccccctgagatcaagtacAgggagtcactgtgcttcgtg 3′
3′ cgggggactctagttcatgTccctcagtgacacgaagcac 5′
                                        ccctcagtgacacgaagcac *
                                      3′ adjacent primer 5′
                                       (5′ end labelled)

| PCR amplification using
↓ dGTP, dATP, dCTP and dUTP

5′ gccccctgagatcaagtacAgggagucacugugcuucgug 3′
3′ cgggggacucuaguucaugUccctcagtgacacgaagcac 5′ *

| Removal of primers not utilised
| in amplification and incubation
↓ with Uracil-DNA-Glycosylase (- = AP site)

5′ gccccctgagatcaagtacAgggag-cac-g-gc--cg-g 3′
3′ cgggggac-c-ag--ca-g-ccctcagtgacacgaagcac 5′ *

| Cleavage of AP sites by treatment
↓ with alkali and heat

5′ gccccctgagatcaagtacAgggag cac g gc  cg g 3′
3′ cgggggac c ag  ca g ccctcagtgacacgaagcac 5′ * labelled 20 nucleotide
                              fragment

Denaturing polyacrylamide gel
              electrophoresis and autoradiography

FIG. 1B normal allele

```
  5' distal primer    3'
  gccccctgagatcaagtac
5' gccccctgagatcaagtacGgggagtcactgtgcttcgtgcag 3'
3' cgggggactctagttcatgCccctcagtgacacgaagcacgtc 5'
                            tcagtgacacgaagcacgtc *
                           3' adjacent primer    5'
        position 1021      (5' end labelled)
```

| PCR amplification using
| dGTP, dATP, dCTP and dUTP

```
5' gccccctgagatcaagtacGgggagucacugugcuucgugcag 3'
3' cgggggacucuaguucaugCccctcagtgacacgaagcacgtc 5' *
```

| Incubation with Uracil-DNA-Glycosylase (- = AP site)

```
5' gccccctgagatcaagtacGgggag-cac-g-gc--cg-gcag 3'
3' cgggggac-c-ag--ca-gCccctcagtgacacgaagcacgtc 5' *
```

| Cleavage of AP sites by treatment
| with alkali and heat

```
5' gccccctgagatcaagtacGgggag cac g gc   cg gcag 3'
3' cgggggac c ag  ca gCccctcagtgacacgaagcacgtc 5' *
``` labelled 25 nucleotide
fragment

Denaturing polyacrylamide gel
electrophoresis and autoradiography

FIG. 2A mutant allele

```
     5' distal primer    3'
     gcccccctgagatcaagtac
5' gcccccctgagatcaagtacAgggagtcactgtgcttcgtgcag 3'
3' cggggggactctagttcatgTccctcagtgacacgaagcacgtc 5'
                       tcagtgacacgaagcacgtc *
                       3' adjacent primer    5'
                          (5' end labelled)
```

| PCR amplification using
| dGTP, dATP, dCTP and dUTP

```
5' gcccccctgagatcaagtacAgggagucacugugcuucgugcag 3'
3' cgggggGacucuaguucaugUccctcagtgacacgaagcacgtc 5' *
```

| Incubation with Uracil-DNA-Glycosylase (- = AP site)

```
5' gcccccctgagatcaagtacAgggag-cac-g-gc--cg-gcag 3'
3' cgggggGac-c-ag--ca-g-ccctcagtgacacgaagcacgtc 5' *
```

| Cleavage of AP sites by treatment
| with alkali and heat

```
5' gcccccctgagatcaagtacAgggag cac g gc   cg gcag 3'
3' cgggggGac c ag   ca g ccctcagtgacacgaagcacgtc 5' *
``` labelled 23 nucleotide
fragment

Denaturing polyacrylamide gel
electrophoresis and autoradiography

FIG. 2B normal allele

5' distal primer 3'
gccccccctgagatcaagtic
5' gccccccctgagatcaagtacGgggagtcactgtgcttcgtgcag 3'
3' cggggggactctagttcatgCccctcagtgacacgaagcacgtc 5'
　　　　　　　　　　　　　　 tcagtgacacgaagcacgtc *
　　　　　　　　　　　　3' adjacent primer　　5'
position 1021　　　　　(5' end labelled)

| PCR amplification using
| dGTP, dATP, dCTP and dUTP

5' gccccccctgagatcaagticGggagucacugugcuucgugcag 3'
3' cggggggacucuaguucacgCccctcagtgacacgaagcacgtc 5' *

| Incubation with Uracil-DNA-Glycosylase (- = AP site)

5' gccccccctgagatcaagticGggag-cac-g-gc--cg-gcag 3'
3' cggggggac-c-ag--cacgCccctcagtgacacgaagcacgtc 5' *

| Cleavage of AP sites by treatment
| with alkali and heat

5' gccccccctgagatcaagticGggag cac g gc　cg gcag 3'
3' cggggggac c ag　cacgCccctcagtgacacgaagcacgtc 5' * labelled 28 nucleotide
　　　　　　　　fragment

Denaturing polyacrylamide gel
electrophoresis and autoradiography

FIG. 3A mutant allele

```
        5' distal primer    3'
          gccccctgagatcaagtic
    5' gccccctgagatcaagtacAgggagtcactgtgcttcgtgcag 3'
    3' cgggggactctagttcatgTccctcagtgacacgaagcacgtc 5'
                          tcagtgacacgaagcacgtc *
                         3' adjacent primer    5'
                            (5' end labelled)
```

| PCR amplification using
↓ dGTP, dATP, dCTP and dUTP

```
    5' gccccctgagatcaagticAgggagucacugugcuucgugcag 3'
    3' cgggggacucuaguucacgUccctcagtgacacgaagcacgtc 5' *
```

| Incubation with Uracil-DNA-Glycosylase
↓
                          (- = AP site)

```
    5' gccccctgagatcaagticAgggag-cac-g-gc--cg-gcag 3'
    3' cgggggac-c-ag--cacg-ccctcagtgacacgaagcacgtc 5' *
```

| Cleavage of AP sites by treatment
↓ with alkali and heat

```
    5' gccccctgagatcaagticAgggag cac g gc   cg gcag 3'
    3' cgggggac c ag   cacg ccctcagtgacacgaagcacgtc 5' *
``` labelled 23 nucleotide
fragment

Denaturing polyacrylamide gel
electrophoresis and autoradiography

FIG. 3B normal allele

```
5' distal primer    3'
  gcccccctgagatcaagtic
5' gcccccctgagatcaagtacGgggagtcactgtgcttcgtgcag 3'
3' cggggggactctagttcatgCccctcagtgacacgaagcacgtc 5'
                           tcagtgacacgaagcacgtc *
                        3' adjacent primer    5'
     position 1021       (5' end labelled)
```

| PCR amplification using
| dGTP, dATP, dCTP and dUTP

```
5' gcccccctgagatcaagticGgggagucacugugcuucgugcag 3'
3' cgggggggacucuaguucacgCccctcagtgacacgaagcacgtc 5' *
```

| Incubation with Uracil-DNA-Glycosylase
|                                    (- = AP site)

```
5' gcccccctgagatcaagticGgggag-cac-g-gc--cg-gcag 3'
3' cggggggac-c-ag--cacgCccctcagtgacacgaagcacgtc 5' *
```

| Cleavage of AP sites by treatment
| with heat

```
5' gcccccctgagatcaagticGgggag>cac>g>gc>>cg>gcag 3'
3' cggggggac<c<ag <cacgCccctcagtgacacgaagcacgtc 5' *
                     cacgCccctcagtgacacgaagcacgtc 5' *
``` labelled 28 nucleotide
fragment with and without
3'-terminal deoxyribosephosphate Denaturing polyacrylamide gel
electrophoresis and autoradiography

FIG. 4A mutant allele

```
       5' distal primer     3'
        gcccccctgagatcaagtic
5' gcccccctgagatcaagtacAgggagtcactgtgcttcgtgcag 3'
3' cggggggactctagttcatgTccctcagtgacacgaagcacgtc 5'
                            tcagtgacacgaagcacgtc *
                         3' adjacent primer    5'
                            (5' end labelled)
```

| PCR amplification using
↓ dGTP, dATP, dCTP and dUTP

5' gcccccctgagatcaagticAgggagucacugugcuucgugcag 3'
3' cggggggacucuaguucacgUccctcagtgacacgaagcacgtc 5' *

| Incubation with Uracil-DNA-Glycosylase
↓
(- = AP site)

5' gcccccctgagatcaagticAgggag-cac-g-gc--cg-gcag 3'
3' cggggggac-c-ag--cacg-ccctcagtgacacgaagcacgtc 5' *

| Cleavage of AP sites by treatment
↓ with heat

5' gcccccctgagatcaagticAgggag>cac>g>gc> cg>gcag 3'
3' cggggggac<c<ag <cacg<ccctcagtgacacgaagcacgtc 5' *
                       ccctcagtgacacgaagcacgtc 5' * labelled 23 nucleotide
fragment with and without
3'-terminal deoxyribosephosphate Denaturing polyacrylamide gel
electrophoresis and autoradiography

FIG. 4B normal allele

```
   5' distal primer    3'
   gccccctgigitciigtic
5' gccccctgagatcaagtacGgggagtcactgtgcttcgtg 3'
3' cggggggactctagttcatgCccctcagtgacacgaagcac 5'
                        ccctcagtgacacgaagcac-biotin
                        3' adjacent primer    5'
     position 1021
```

| PCR amplification using
    | dGTP, dATP, dCTP, dUTP and 32P dCTP

5' gccccctgigitciigticGgggagucacugugcuucgug 3'

3' cggggggacccccagcccacgCcc ctcagtgacacgaagcac-biotin-5'

| Immobilisation of amplified DNA sample to
    | strepavidin coated tube A. Removal of
    | complementary target strand by washing
    | with alkali (tube A)

3' cggggggacccccagcccacgCcc ctcagtgacacgaagcac-biotin-5'

| Incubation with Uracil-DNA-Glycosyalse
    | and cleavage of AP sites by treatment
    | with alkali and heat (tube A)

3' cggggggacccccagcccacgCcc ctcagtgacacgaagcac-biotin-5'

| Removal of released material to tube B (tube A)

3' cggggggacccccagcccacgCcc ctcagtgacacgaagcac-biotin-5'

FIG. 5A mutant allele

```
      5' distal primer    3'
    gccccctgigitciigtic
5'  gccccctgagatcaagtacAgggagtcactgtgcttcgtg 3'
3'  cggggggactctagttcatgTccctcagtgacacgaagcac 5'
                        ccctcagtgacacgaagcac-biotin
                      3' adjacent primer    5'
                         (5' end labelled)
```

| PCR amplification using
| dGTP, dATP, dCTP, dUTP and 32P dCTP

```
5' gccccctgigitciigticAgggagucacugugcuucgug 3'
3' cggggggaccccagcccacgUccctcagtgacacgaagcac-biotin-5'
```

| Immobilisation of amplified DNA sample to
| strepavidin coated tube A. Removal of
| complementary target strand by washing
| with alkali (tube A)

```
3' cggggggaccccagcccacgUccctcagtgacacgaagcac-biotin-5'
```

| Incubation with Uracil-DNA-Glycosyalse
| and cleavage of AP sites by treatment
| with alkali and heat (tube A)

```
3' cggggggaccccagcccacg ccctcagtgacacgaagcac-biotin-5'
```

| Removal of released material to tube B (tube B)                                    (tube A)

```
3' cggggggaccccagcccacg ccctcagtgacacgaagcac-biotin-5'
```

FIG. 5B

M. tuberculosis MPB70 gene

```
Primer A
  (21n)
   ────▶├──11n──┤
─────────────────────u─────//──────────────────────────
  320                          ─────u─────────────  436
                                    ├2n┤◀────
                                        Primer B (21n)
└─────────────────116 bp─────────────────┘
```

```
Primer C
  (21n)
   ────▶├────26n────┤
─────────────────────u─────//──────────────────────────
  551                          ─────u─────────────  681
                                    ├2n┤◀────
                                        Primer D (21n)
└─────────────────130 bp─────────────────┘
```

FIG. 8

GLYCOSYLASE MEDIATED DETECTION OF NUCLEOTIDE SEQUENCES AT CANDIDATE LOCI

This application is the national phase under 35 U.S.C. §371 of prior PCT International Application No. PCT/IE95/00067 which has an International filing date of Dec. 21, 1995 which designated the United States of America, the entire contents of which are hereby incorporated by reference.

TECHNICAL FIELD

This invention relates to a method for rapidly detecting the presence or absence of a particular nucleic acid sequence at a candidate locus in a target nucleic acid sample. In particular, the invention relates to a method for detecting specific mutations in a DNA sample.

BACKGROUND ART

Detection of specific sequences at candidate loci in target nucleic acid samples is highly important for several reasons relating to diagnosis of inherited disorders and of infectious diseases. Detection of multiple different mutations is necessary for screening for the presence of specific gene tic disorders. Detection of specific sequences in amplified DNA samples significantly enhances current DNA diagnostic methods for the detection of organisms of interest and especially of infectious organisms. Current techniques for the detection of sequences at candidate loci are either cumbersome, lacking in specificity, difficult to optimise and use or poorly adaptable to high sample throughput.

There are several methods known for the detection of a particular nucleic acid sequence at a candidate locus in a target nucleic acid sample. Details of these methods are as follows.

1) Restriction enzyme analysis

Detection of a particular DNA sequence by restriction enzyme analysis. Restriction enzymes cleave DNA at specific sequences. For example, the enzyme EcoRI cleaves double stranded DNA at the sequence GAATTC. Thus, by checking a candidate locus in a particular DNA sample for cleavage with EcoRI, one may deter mine whether the sequence GAATTC is present or absent at the candidate locus. The appearance or disappearance of a restriction site from a candidate locus indicates that one or more of the bases in the sequence at the candidate locus has been altered. Thus, the creation or loss of a restriction site at a candidate locus can involve the alteration of any base or bases of the respective restriction site. Therefore, the appearance or disappearance of a restriction site at a candidate locus may not inform the investigator of the exact sequence change. However, there are a number of problems with the use of restriction enzymes for the detection of specific sequences at candidate loci. These include:

a) the presence or absence of a specific sequence at a candidate locus regularly does not occur at a restriction site;

b) since different restriction enzymes have different recognition sequences, different restriction enzymes are regularly required for the detection of the presence or absence of a particular sequence at different candidate loci; and c) because different enzymes can be required for the detection of the presence or absence of a particular sequence at different candidate loci, a high throughput is difficult to achieve with this approach and automation is difficult.

2) DNA sequencing

DNA sequencing allows detection of a particular sequence at any candidate locus. The main methods of DNA sequencing are the Sanger method (Sanger, F. and Coulson, A. R. (1975) J. Mol. Biol. 94, 444–448), also known as the dideoxy method or chain termination method, and the Maxam Gilbert method (Maxam, A. M. and Gilbert, W. (1977) Proc. Natl. Acad. Sci. USA 74, 560–564), also known as the chemical method.

While DNA sequencing is the ultimate way of determining if a particular sequence is presence or absence at a particular candidate locus, it suffers from a number of drawbacks as follows:

a) it is a cumbersome and difficult method for routine detection of the presence or absence of a particular sequence at different candidate loci;

b) full size sequencing gels are required for determination of the presence or absence of a particular sequence at a given candidate locus;

c) the DNA sample for analysis needs to be of high quality in order to obtain good quality DNA sequences;

d) DNA sequencing of directly amplified DNA samples is regularly problematic;

e) sequencing gels can often be difficult to read;

f) high throughput with a high success rate is difficult to achieve;

g) some DNA sequences are more difficult to obtain than others; and h) resolution of multiple DNA fragments of different size is necessary to detect the presence or absence of a specific sequence at a candidate locus.

3) Uracil interference

A method has been described whereby uracil is incorporated into an amplified DNA molecule randomly and at a low level. This is achieved by amplifying the DNA in the presence of the normal DNA precursor nucleotides and dUTP. The ratio of dTTP to dUTP is chosen so that in the amplification process dUTP is occasionally incorporated opposite an adenine residue on the template strand while dTTP is incorporated opposite adenine residues at a much higher frequency. This results in a population of products bearing a low level of uracil residues randomly distributed throughout the amplified molecules. Treatment of the amplified products with uracil glycosylase and cleavage of the abasic site results in cleavage of the molecules at the position of incorporation of the uracil residues. Because the uracil was incorporated randomly opposite adenine residues at a low level, different molecules will be cleaved at different points depending on where the uracil residues were incorporated. Thus labelling of one of the primers used in the amplification process and separation of all of the cleavage products on a DNA sequencing gel produces a ladder of fragments that allows the determination of the total number of positions of uracil incorporation in one strand of the amplified DNA sample (Tu, W. T. and Struhl, K. Nuc. Acids Res., (1992) 20, 771–775. Devchand P. R. et al., Nuc. Acids Res. (1993) 21, 3437–3443).

The main application of the approach outlined has been for DNA footprinting (a method used to identify the bases in DNA to which particular proteins bind).

The uracil incorporation method can be used to determine the location of the total number of uracil residues in an amplified DNA sample. However, a) it would be a cumbersome and difficult method for rapid detection of an uracil residue at a specific candidate locus:

b) full size sequencing gels would be required for determination of an uracil residue at a specific candidate locus;

c) sequencing gels can often be difficult to read/interpret; and d) resolution of multiple DNA fragments of different size would be necessary to detect an uracil residue at a specific candidate locus.

4) Use of mismatched nucleotide glycosylases

Two accounts of the use of mismatched nucleotide glycosylases have been reported for detection of point mutations (Lu, A-L and Hsu, I-C, Genomics (1992) 14, 249–255 and Hsu, I-C., et al, Carcinogenesis (1994)14, 1657–1662). The glycosylases in question are the *E. coli* Mut Y gene product which releases the mispaired adenines of A/G mismatches efficiently and A/C mismatches inefficiently by regular glycosylase action and the human thymidine DNA glycosylase which cleaves at Gfr mismatches. These enzymes have been used for mutation detection in amplified heteroduplex DNA molecules where mismatches are present. Labelling of one of the primers used in the amplification reaction permits detection of the position of the mismatch after glycosylase treatment, cleavage of the abasic site and resolution of the fragments by gel electrophoresis.

There are several problems with this method as follows:

a) the method is dependent on the formation of heteroduplex molecules where a mismatched based pair is formed at the site in question. Thus, to detect a mutation in a homozygous sample, an external probe must be provided and hybridization carried out to generate the mismatch;

b) the method permits detection of the position of the mismatch but not necessarily the sequence at the mismatch; and c) not all mismatches are recognised with equal efficiency.

5) Other methods based on cleavage of mismatched base pairs

Several other methods based on the cleavage of mismatched base pairs have been described for detecting point, deletion and insertion type mutations. These include chemical cleavage at mismatched base pairs, heteroduplex detection based on the slower migration thereof during gel electrophoresis relative to homoduplex molecules which migrate faster. RNAse cleavage of mismatches in RNA:DNA hybrids and cleavage of mismatches by enzymatic means.

All of the above methods can detect mutations in heteroduplex molecules and allow the approximate position of the mutation in the nucleic acid molecule to be determined (except in the case of the heteroduplex electrophoresis retardation method which only informs of the presence of a mutation in the sample). However, these methods only work on heteroduplex DNA and do not allow one to deduce what specific sequence is present at a candidate locus.

6) Ligase chain reaction

The ligase chain reaction (LCR) is a probe amplification method that can be used for detecting the presence or absence of a particular target sequence at a candidate locus. It utilises the enzyme DNA ligase to join two pairs of oligonucleotides that hybridise adjacent to one another on the denatured target DNA strands. The enzyme forms a phosphodiester link between the two oligonucleotides, provided that the oligonucleotides at the junction correctly hybridised with the template. Thus an exact match between the oligonucleotides and the target sequence at the junction permits ligation of the oligonucleotides resulting in the formation of a larger product which is the cumulative size of both the oligonucleotides. Multiple cycles of annealing, ligation and denaturation results in the exponential amplification of the larger product. Thus detection of the larger product indicates the presence of a sequence at the candidate locus while absence of the larger product means that there were differences between the oligonucleotide sequences and the sequence of the template DNA.

While this method has good potential for detecting particular sequences at candidate loci and also offers high throughput of samples, it does not allow one to deduce what specific sequence is present at a candidate locus. In addition, the method requires considerable effort to optimise the process.

7) ARMS method

By designing appropriate primers for use in the polymerase chain reaction, it is possible to detect the presence or absence of a specific sequence at a candidate locus. In this method known as the amplification refractory method (ARMS), primers are designed so that amplification of a target sequence only occurs if there is a perfect match between the 3' end of the primers and the target sequence. Thus if a pair of primers are designed so that one primer is complementary to a given sequence of the target sample while the partner primer is designed so that its 3' end is complementary to the wild type sequence at the candidate locus, then this pair of primers will only produce a product on amplification if the wild type sequence is present at the candidate locus. If a third partner primer is designed so that its 3' end is complementary to the mutant sequence at the candidate locus, then this primer if used with the primer complementary to the given sequence of the target sample will only produce a product on amplification if a mutant sequence is present at the candidate locus. This method suffers from a number of problems as follows:

a) three primers are required to determine whether wild type or mutant sequence is present at the candidate locus;

b) the method does not allow one to deduce what specific sequence is present at a candidate locus; and c) the annealing conditions for the ARMS method have to precise, thus the method is difficult to transfer in many cases and has to be optimised for each mutation investigated.

Thus, it will be appreciated that there is a need in the nucleic acid diagnostics field for a robust method for detection of specific sequences at candidate loci that allows rapid and high throughput of samples.

Methods in Molecular Biology, Vol. 9, 1991, p51–68 describes various rapid methods for detecting polymorphic markers in DNA. The polymorphisms are detected by amplification of the DNA surrounding and including the locus of interest and mismatch detection at that locus. One of the methods involves cleaving the DNA phosphate linkages at sites of mismatches following modification and subsequently analysing the cleavage products so as to identify the presence or absence of a particular polymorphism in the genomic DNA. The alternative methods described therein rely on the differential hybridisation and/or extension of oligonucleotide primers to sites of polymorphisms dependent on whether a mismatched base pair is generated during the hybridisation step. These methods rely on analysing the hybridised or amplified products so as to identify the presence or absence of a particular polymorphism in the genomic DNA. The methods described do not involve the introduction of a modified base, which is a substrate for a DNA glycosylase, into the amplified DNA and do not involve the excision of such a modified base by the DNA glycosylase.

DISCLOSURE OF INVENTION

The invention provides a method for rapidly detecting the presence or absence of a particular nucleic acid sequence at a candidate locus in a target nucleic acid sample which comprises the steps of:

i) introducing a modified base which is a substrate for a DNA glycosylase into said candidate locus at one or more preselected positions;

ii) excising the modified base by means of said DNA glycosylase so as to generate an abasic site;

iii) cleaving phosphate linkages at abasic sites generated in step ii); and iv) analysing the cleavage products of step iii) so as to identify in said target nucleic acid sequence the presence or absence of said particular nucleic acid sequence at said candidate locus.

The method according to the invention offers significant advantages over existing methods in that a single enzyme and a single process can be used to detect multiple known mutations in DNA. Thus, a large throughput of sample can be achieved rapidly and easily as hereinafter demonstrated.

The method in accordance with the invention enables one to investigate a target nucleic acid to determine if a particular sequence, such as a gene mutation is presence or absent at a particular location known as the "candidate locus" herein.

Preferably, the candidate locus is amplified using normal DNA precursor nucleotides and at least one modified precursor nucleotide.

The term "amplifying" as used herein refers to any in vitro process for increasing the number of copies of a nucleotide sequence or sequences. Amplification of a target sample results in the incorporation of precursor nucleotides into the DNA being amplified. Typically, amplification of a target sample is carried out using appropriate primers in the polymerase chain reaction (PCR). Amplification of a target sample may be also carried out using the ligase chain reaction (LCR) and a variation of the LCR which employs a short PCR step (PLCR). Precursor nucleotides in the case of a DNA amplification process refer to the deoxyribonucleotides dATP, dCTP, dGTP and dTTP herein referred to as "normal" DNA precursor nucleotides. Modified precursor nucleotide(s) as used herein refers to a modified nucleotide or nucleotides that can be incorporated into a nucleic acid so that a substrate base or bases (glycosylase substrate base) is generated which is recognised by a DNA glycosylase enzyme.

The amplification will typically involve amplifying a target nucleic acid sample using a combination of normal DNA precursor nucleotides and one or more modified precursor nucleotide(s) where the modified precursor nucleotide replaces one of the normal precursor nucleotides. The incorporation of a modified precursor nucleotide into the amplified product generates one or more glycosylase substrate base(s) at one or more positions recognised by a DNA glycosylase enzyme in the amplified product. A particular sequence may be present at the candidate locus in all or a portion of the target nucleic acid sample, or may be absent from the target nucleic acid sample.

Further, preferably, at least one of the primers for the amplification is positioned adjacent to the candidate locus.

Thus, suitably primers for amplification purposes are designed such that one of the primers is positioned adjacent (referred to as the "adjacent primer" herein) to the candidate locus so that during the amplification process, the position of incorporation of the first modified precursor nucleotide into the extended adjacent primer will be at, or distal to, the candidate locus depending on the particular sequence present at the candidate locus. The other primer of a pair of primers as used herein is referred to as the "distal primer" as hereinafter defined.

Design of the adjacent and distal primers so that the modified precursor nucleotide is incorporated at the candidate locus alone or not incorporated at all, if a particular sequence is present or absent in the amplified target nucleic acid sample, permits cleavage of the target strand bearing the glycosylase substrate base into two fragments.

Amplification of the target strand of the target sample can be achieved using the adjacent oligonucleotide primer which anneals to the complementary region of the complementary target strand of the target nucleic acid sample. Primer extension of the adjacent primer in the amplification process results in the incorporation of precursor nucleotides and modified precursor nucleotides in a 5' to 3' direction. The amplified DNA strand generated through the extension of the adjacent primer in the amplification process is referred to as the "target strand" herein. The amplified DNA strand generated through the extension of the other primer (referred to as the "distal primer" herein) in the amplification process is referred to as the "complementary target strand" herein. Amplification of the complementary target strand of the target sample can be achieved using the distal oligonucleotide primer which anneals to the complementary region of the target strand of the target nucleic acid sample. Primer extension of the distal primer in the amplification process results in the incorporation of precursor nucleotides and modified precursor nucleotides in a 5' to 3' direction. Amplification of both strands of the target sequence can be achieved using both the adjacent and distal primers. In the PCR process, repeated cycles of amplification are performed. The size of the amplified fragment in this case is delineated by the position of annealing of the adjacent and distal primers to the strands of the target nucleic acid sample.

For detection of a particular sequence such as a mutation at the candidate locus in a target sample, primers for amplification purposes are designed so that the adjacent primer is positioned close to the candidate locus so that during the amplification process, the position of the first modified precursor nucleotide incorporated into the extended adjacent primer will be at, or distal to, the candidate locus depending on whether a particular sequence is present or absent at the candidate locus. In cases where the incorporation of a sole modified precursor nucleotide at the candidate locus is desirable, the primers are designed so that all of the bases in the primers promote preferential incorporation of nucleotides other than the key modified precursor nucleotide (the key modified precursor nucleotide being the modified precursor nucleotide to be incorporated at the candidate locus depending on the presence or absence of a particular sequence) in the newly synthesised DNA complementary to the primer sequences. For example, in the case where dUTP is the modified precursor nucleotide, the primers are synthesised so that the adenine bases are replaced by cytosine, guanine, thymine, inosine or modified bases (other than uracil) which preclude incorporation of uracil residues in the newly synthesised DNA complementary to the primer sequences. In the case where dITP is the modified precursor nucleotide, the primers are synthesised so that the cytosine bases are replaced by guanine, thymine, adenine, uracil or modified bases (other than inosine) which preclude incorporation of inosine residues in the newly synthesised DNA complementary to the primer sequences. In cases where cleavage at specific points in the primers is desirable in addition to cleavage at the candidate locus on the target strand, the primers are synthesised so that one or more glycosylase substrate base(s) is/are present in the primer at a defined position or positions. Treatment of the primer with the appropriate glycosylase after the amplification process will result in cleavage of the primers at a specific position or positions. Design of the primers in such a fashion facilitates detection of specific fragments of the target strand indicative of the presence or absence of a particular sequence at the candidate locus and serves to reduce the size of primers if desirable so that they do not interfere with the detection process.

Suitably at least one primer is labelled when an amplification method is used in accordance with the invention. Labelling of one of the primers prior to the amplification process allows detection of the amplified target or complementary strand alone. Labelling of the primers can be performed by a variety of means including addition of a radioactive, fluorescent, or detectable ligand to the primer during or post primer synthesis. The use of a labelled precursor nucleotide (i.e. a radioactive precursor nucleotide, or a precursor nucleotide with a linked fluorescent or detectable ligand group) in the amplification process facilitates detection of the target stand and the complementary target strand and any DNA fragments arising from the glycosylase mediated cleavage process that bear the incorporated label. DNA staining methods such as silver or ethidium bromide staining facilitates detection of all of the fragments generated as a result of the glycosylase mediated cleavage of the amplified target nucleic acid sample after separation of the fragments. Alternatively, detection of the amplified target and complementary strand and fragments generated as a result of the glycosylase mediated cleavage can be accomplished using appropriate nucleic acid hybridisation probes.

The modified base can be introduced by chemical modification of an existing base at the candidate locus.

Several methods exist where treatment of DNA with specific chemicals modify existing bases so that they are recognised by specific DNA glycosylase enzymes. For example, treatment of DNA with alkylating agents such as methylnitrosourea generates several alkylated bases including N3-methyladenine and N3-methylguanine which are recognised and excised by alkyl purine DNA-glycosylase. Treatment of DNA with sodium bisulfite causes deamination of cytosine residues in DNA to form uracil residues in the DNA which can be cleaved by uracil DNA-glycosylase.

Thus, from knowledge of the prior art, bases present at the candidate locus of an amplified target nucleic sample can be converted into glycosylase recognisable substrates by chemical means. For example, a cytosine present at the candidate locus can be readily converted into an uracil, thereby rendering the amplified sample susceptible to uracil DNA-glycosylase cleavage at the candidate locus. If the adjacent primer is synthesised so that it contains 5-methylcytosine rather than cytosine in such a case, the primer will be resistant to uracil DNA-glycosylase mediated cleavage since deamination of 5-methylcytosine generates a thymine residue rather than an uracil residue.

Preferably, the modified base is excised (or cleaved) by means of a DNA glycosylase enzyme.

Thus, suitably following the amplification process, the amplified product is treated with a suitable DNA glycosylase enzyme which recognises and releases the glycosylase substrate bases present in the amplified target sample and consequently generates apurinic or apyrimidinic sites in the amplified target nucleic acid sample.

In the case where the modified precursor nucleotide is dUTP, the glycosylase substrate base uracil will be generated in the amplified target nucleic acid sample. Addition of uracil DNA-glycosylase to the sample releases the uracil from the sample. In the case where the modified precursor nucleotide is dITP, the glycosylase substrate base hypoxanthine will be generated in the amplified target nucleic acid sample. Addition of alkylpurine DNA-glycosylase to the sample releases the hypoxanthine from the sample. Release of the glycosylase substrate bases from the amplified target nucleic acid sample results in an apyriridinic site in the case of uracil and an apurinic site in the case of hypoxanthine.

Glycosylase mediated cleavage of the target strand of an amplified target nucleic acid sample as a result of a particular sequence being present or absent at the candidate locus in the amplified target nucleic acid also permits detection by immobilisation methods. In this instance one of the primers usually the adjacent primer is synthesised with a "capture" agent attached which allows immobilisation of the target strand to a solid matrix. The primers are designed so that the modified precursor nucleotide is incorporated at the candidate locus alone in the amplified target nucleic acid sample. The amplification process is carried out in the presence of a labelled precursor nucleotide resulting in the incorporation of label into the extended adjacent primer distal (3') to the candidate locus. Immobilisation of the amplified target strand is achieved by incubating the amplified target strand with a solid matrix bearing a molecule which binds the capture agent specifically. Removal of the complementary target strand is then performed by washing with a denaturating agent and removing all of the non-immobilised material. If a glycosylase substrate base is present at the candidate locus, release of the labelled portion of the target strand will occur in the glycosylase mediated cleavage process. Removal of the released fragment and determination of the level of label released or remaining immobilised is diagnostic of the presence or absence of the particular sequence at the candidate locus. Alternatively, if labelling of the target strand is not desirable, detection may be performed by use of specific nucleic acid hybridisation probes. Such probes can be readily designed to detect the complete immobilised target strand, the portion of the target strand released after the glycosylase mediated cleavage process or the portion of the target strand remaining after the cleavage process.

This glycosylase mediated cleavage process allows the detection of any particular sequence at a candidate locus in any target sample provided the DNA sequence surrounding the mutation site is known. Sequence information of at least 15 to 20 nucleotides on each side of the candidate locus is required in order to design appropriate primers for the amplification process.

The use of a DNA glycosylase enzyme which recognises a modified base has not previously been used directly for the detection of a particular sequence at a candidate locus in an amplified target nucleic acid sample.

A main application of the glycosylase mediated cleavage process is that it permits detection of the presence or absence of a particular sequence at a candidate locus by the aforementioned immobilisation methods.

A suitable "capture" agent is biotin. Thus, one of the primers is suitably synthesised with biotin attached which allows immobilisation of the target strand to streptavidin coated on, or linked to a solid matrix so as to allow immobilisation of the target strand. The primers are designed so that the modified precursor nucleotide is only incorporated in the target strand at the candidate locus alone if a particular sequence is present or absent at the candidate locus.

Suitably one of the precursor nucleotide(s) is also labelled. As indicated above the amplification process is preferably carried out in the presence of a labelled precursor nucleotide, such as an alpha $P^{32}$ dNTP, a fluorescent dNTP or digoxygenin dNTP resulting in the incorporation of the label into the extended adjacent primer. The primer bearing the capture groups is also designed so that the labelled precursor nucleotide(s) can only be incorporated distal to (3') the primer in question and the candidate locus i.e. the labelled precursor nucleotide cannot be incorporated between the candidate locus and the adjacent primer.

Preferably the phosphate linkages at the abasic sites are cleaved by a treatment selected from alkali treatment or other chemical treatment, heat treatment and treatment with an enzyme.

The process of strand cleavage resulting from the release of glycosylase substrate base by DNA glycosylase action followed by abasic site cleavage is referred to herein as glycosylase mediated cleavage. The presence or absence of a particular sequence at the candidate locus results in the incorporation, or lack of incorporation of a modified precursor nucleotide at the candidate locus in the amplified target nucleic acid sample. Thus if a modified precursor nucleotide is incorporated at the candidate locus, cleavage of the target strand will occur at the candidate locus through the glycosylase mediated cleavage process and this cleavage point will be the closest cleavage point to the 3' end of the extended adjacent primer. If a modified precursor nucleotide is not incorporated at the candidate locus, the closest cleavage point to the 3' end of the extended adjacent primer will occur at the first point distal to the candidate locus where a modified precursor nucleotide is incorporated. Therefore the observed length of the extended adjacent primer following the glycosylase mediated cleavage process will be diagnostic of the presence or absence of the particular sequence at the candidate locus.

The preferred treatment is alkali at high temperature, or with an enzyme which cuts specifically at apurinic or apyridimic sites, such as E. coli endonuclease IV. Both of these treatments cleave the apurinic or apyridimic site to completion on the 5' side. In a case where there is a sole glycosylase substrate base at the candidate locus in the amplified target strand, glycosylase mediated cleavage cuts the target strand at a single position yielding two fragment strands. Manipulation of the design of the primer sequences used permits amplification of products bearing glycosylase substrate bases at any desired position(s) on the target and/or complementary strand in addition to the candidate locus on the target strand and facilitates subsequent analysis of the glycosylase cleaved amplified target nucleic acid sample.

The presence or absence of a particular sequence at the candidate locus determines whether or not a glycosylase substrate base is incorporated at the candidate locus in the target strand. Thus different diagnostic cleavage patterns are produced by glycosylase mediated cleavage of an amplified target strand depending on whether the particular sequence is present or absent at the candidate locus. Primers may also be designed so that glycosylase substrate bases are absent from the target strand if a particular sequence is present at the candidate locus. In such a case, the target strand is resistant to glycosylase mediated cleavage.

The products/cleavage pattern resulting from the glycosylase mediated cleavage of the amplified target nucleic acid sample may be discerned by existing DNA sizing methods such as polyacrylamide gel electrophoresis, agarose gel electrophoresis or high performance liquid chromatography (HPLC).

Thus, the size of the extended adjacent primer when an amplification method is used in accordance with the invention can be determined after denaturation by existing DNA sizing methods such as denaturating polyacrylamide gel electrophoresis. Labelling of the adjacent primer prior to the amplification process facilitates detection of the cleaved extended adjacent primers alone while the use of a labelled precursor nucleotide in the amplification process or DNA staining methods facilitated detection of all of the fragments generated as a result of glycosylase mediated cleavage of the amplified target nucleic acid sample.

The modified base used is preferably uracil or hypoxanthine.

Thus, the preferred modified precursor nucleotides are dUTP and dITP which when incorporated into DNA generate the glycosylase substrate bases uracil and hypoxanthine respectively. The modified precursor nucleotide dUTP is a base sugar phosphate comprising the base uracil and a sugar phosphate moiety. The modified precursor nucleotide dITP is a base sugar phosphate comprising the base hypoxanthine and a sugar phosphate moiety. Uracil in DNA is recognised specifically by uracil DNA-glycosylase (UDG) and released from DNA. Uracil DNA glycosylase also recognises certain other uracil related bases when present in DNA. Hypoxanthine is recognised specifically by alkylpurine DNA glycosylase (ADG) and released form DNA. This enzyme also recognises and releases N3 methyl adenine. N3 methyl guanine, O2 methyl cytosine and O2 methyl thymine when present in DNA. Amplification of a target DNA sequence using the precursor nucleotides dATP, dCTP and dGTP and the modified precursor nucleotide dUTP results in an amplified DNA where thymine is replaced uracil. The uracil is incorporated in the newly synthesised DNA strand at positions complementary to adenine residues in the template DNA strand during the amplification process. Amplification of a target DNA sequence in the presence of the precursor nucleotides dATP, dCTP and dTTP and the modified precursor nucleotide dITP results in an amplified DNA where guanine is preferentially replaced by hypoxanthine. The hypoxanthine is preferentially incorporated opposite cytosines in the template DNA strand in the amplification process when the other precursor nucleotides are not limiting.

Any DNA or RNA from any source can serve as a target sample.

Preferably, the target nucleic acid sample is DNA. For amplification purposes, RNA is first converted into cDNA by reverse transcription. A particular sequence may be present at the candidate locus in all or a portion of the target nucleic acid sample, or may be absent from the target nucleic acid. The target nucleic acid sample may be homozygous or heterozygous for the presence or absence of a particular sequence at the candidate locus which is one of the advantages of the method according to the invention over some of the prior art methods discussed above.

The DNA which can be used in accordance with the method of the invention can be single stranded, homoduplex or heteroduplex DNA.

Some of the advantages of the present invention relative to specific prior art methods are as follows.

The invention has advantages over the restriction enzyme analysis method given that a minimum of two glycosylases are required to identify all possible sequence changes due to mutations such as point, insertion or deletion type mutations at a candidate locus and one glycosylase can be used to detect 10 out of all 12 possible point mutations.

The method according to the invention is significantly faster than DNA sequencing in that full size DNA sequencing type gels are not necessary for sizing the cleavage products and the number of cleavage products that need to be detected to determine if a specific sequence is present or absent in a target nucleic acid is small. Usually, the appearance or disappearance of a single additional DNA fragment in addition to the wild type fragment will be sufficient to diagnose the presence or absence of the particular DNA sequence in the target nucleic acid. By contrast in DNA sequencing, resolution of multiple DNA fragments of different size is necessary to detect the presence or absence of a specific sequence at a candidate locus. The method according to the invention allows the detection of the presence or absence of a specific sequence at a candidate locus by determining whether a DNA fragment is released or not from an immobilised target nucleic acid. This is not possible with DNA sequencing.

The method according to the invention also represents a significant improvement over the uracil interference method. The method according to the invention differs from the uracil interference method in that the modified nucleotide introduced into the target nucleic acid sample is introduced at all preselected positions whereas in the case of the uracil interference method uracil is incorporated randomly and at a low level in the amplified molecules. Also in the case of the method according to the invention the modified nucleotide introduced replaces a particular DNA precursor, while in the uracil interference method a ratio of modified nucleotide to normal nucleotide is used. Other advantages of the method according to the invention relative to the uracil interference method are that the method according to the invention is significantly faster, full size DNA sequencing gels are not necessary for sizing the cleavage products, and the number of cleavage products that need to be detected is small. Usually, the appearance or disappearance of a single additional DNA fragment in addition to the wild type fragment will be sufficient to diagnose the presence or absence of the particular DNA sequence in the target nucleic acid. By contrast in the uracil interference method, resolution of multiple DNA fragments of different size would be necessary to detect an uracil residue at a specific candidate locus. The method according to the invention allows the detection of the presence or absence of a specific sequence at a candidate locus by determining whether a DNA fragment is released or not from an immobilised target nucleic acid. This is not possible with the uracil interference method.

Advantages of the method according to the invention relative to use of mismatched nucleotide glycosylases are that external probes are not required to detect the presence or absence of a particular sequence (a mutation or otherwise) in a homozygous or heterozygous state. In the method according to the invention certain glycosylases such as uracil DNA-glycosylase work on single stranded DNA so that single stranded DNA can be investigated. Furthermore, the modified bases used in accordance with the invention are recognised and removed efficiently by the glycosylase enzymes which recognise them. Thus the invention offers significant advantages over the mismatch cleavage method outlined about in that the provision of external probes is not necessary, no hybridisation steps are required, single stranded DNA can be used and high throughput of samples can be achieved rapidly and easily.

Finally, the method according to the invention has significant advantages over the ARMS method in that only one amplification reaction is necessary to determine whether wild type or mutant sequence is present at the candidate locus. The annealing conditions for the ARMS method have to precise, thus the method is difficult to transfer in many cases and has to be optimised for each mutation investigated. By contrast the method according to the invention is robust, and is optimised easily and enables one achieve a high throughput of samples.

BRIEF DESCRIPTION OF DRAWINGS

FIG. 1 is a schematic representation of procedure A) described in Example 1;

FIG. 2 is a schematic representation of procedure B) described in Example 1;

FIG. 3 is a schematic representation of the procedure described in Example 2;

FIG. 4 is a schematic representation of the procedure described in Example 3;

FIG. 5 is a schematic representation of the procedure described in Example 4;

FIG. 8 is a schematic representation of the procedure described in Example 7.

MODES FOR CARRYING OUT THE INVENTION

Figure 6:
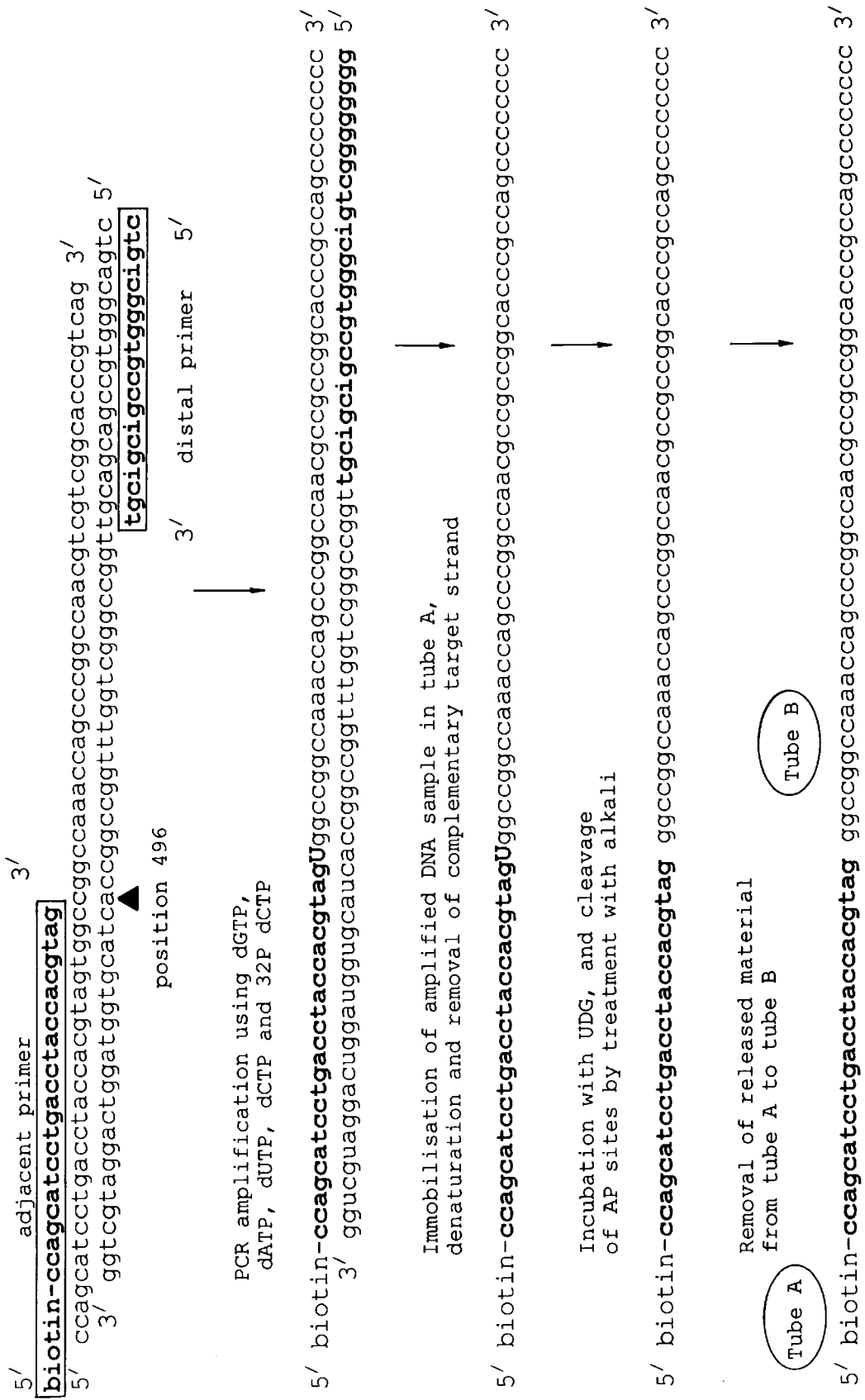
FIG. 6 is a schematic representation of the procedure described in Example 5.

The invention will be further illustrated by the following Examples.

EXAMPLE 1

The method according to the invention was used to detect the presence of a G to A base substitution mutation causal of malignant hyperthermia at position 1021 of the human skeletal ryanodine receptor gene (RYR1) in a patient heterozygous for the mutation. The sequence of steps is depicted in FIG. 1. In this case, the target nucleic acid was DNA extracted from a patient with malignant hyperthermia, the candidate locus was nucleotide 1021 in the human RYR1 gene and the objective was to determine whether the particular sequence base pair G:C or A:T was present at the candidate locus in either RYR1 allele in the patient. The lower strand shown in FIG. 1 is the target strand and the presence or absence of a T (U) nucleotide at the candidate locus was determined. The upper strand is the complementary target strand.

In the context of the Example the normal allele refers to the RYR1 allele bearing the normal sequence and the mutant allele refers to the RYR 1 allele bearing the mutant sequence at position 1021. The DNA sequence surrounding the mutation site is shown in FIG. 1, with the mutation site indicated by a bold upper case letter.

A) The sequence of the target nucleic acid at the candidate locus region and the sequence of the adjacent and distal primers (primers contain standard nucleotides (dG, dA, dT and dC)) are shown in FIG. 1. Six pmoles of the adjacent primer was end-labelled by incubation with 1 unit of polynucleotide kinase, appropriate buffer and 1 uCi$\gamma^{32}$P ATP (3000 Ci/mmol) for 30 min at 37° C. The target nucleic acid sample was amplified by PCR as follows: the reaction mix for PCR contained 200 ng genomic DNA from the affected patient, 0.2 mM dATP, dCTP, dGTP and dUTP, 1.5 mM MgCl$_2$, 50 mM KCl, 10 mM Tris-HCl pH 9.0,0.1% TritonX-100, 6 pmoles of each primer in a total volume of 19 $\mu$l. The reaction mix was then overlaid with an equal volume of mineral oil and a hot start PCR was performed wherein the reaction mix was heated to 94° C. for 5 min prior to addition of 1 unit of Taq polymerase (bringing the total volume to 20 μl). 30 Cycles of 94° C. for 60 sec., 59° C. for 60 sec. and 72° C. for 60 sec. were carried out in thermocycler followed by removal of the aqueous reaction mixture to a separate microtube. The reaction mixture bearing the amplified target nucleic acid was then treated with exonuclease I to digest the primers not extended in the amplification step. This was achieved by incubating 2 μl of the PCR reaction with 0.5 units of exonuclease I at 37° C. for 30 min. The exonuclease was subsequently heat inactivated by incubating the reaction at 80° C. for 15 min.

Uracil DNA glycosylase (0.05 units) was then added and the incubation continued at room temperature for 30 min. Following Uracil DNA glycosylase treatment, the apurinic and apyrdimic (AP) sites generated in the amplified product were cleaved to completion by adding NaOH to a final concentration of 0.25 M and heating the mixture for 15 min at 95° C. The reaction was then neutralised by addition of Tris base to 30 mM final concentration.

An equal volume of formamide loading dye (90% formamide, 0.025% Bromophenol blue, 0.025% Xylene cylanol) was added to the sample which was then heated at 85° C. for 5 min. All of the sample was then loaded onto a 20% denaturing (7 M urea) polyacrylamide gel and electrophoresis was carried out for 3–4 hours at 400 volts for size analysis of the cleaved products in the sample. Following electrophoresis, autoradiography was carried out by exposing the gel directly to X-ray photographic film for 12 hours at −70° C. A labelled set of oligonucleotides (20 mer, 22 mer, 24 mer) was used as markers. Analysis of the autoradiographed products showed that two cleavage products were present in approximately equal amounts. One product was 22 nucleotides (n) in length, corresponding to the normal allele, while the second product corresponding to the mutant allele, was 20n in size, as hereinafter described.

The 20n product could only have been generated if an uracil residue was incorporated at position 1021 in the target strand. Thus the detection of a 20n fragment is diagnostic of the presence of a T residue at position 1021. In the normal allele the first uracil incorporated should be at position 1019 and should result in a 22n product. Thus the detection of a 22n fragment is diagnostic of the absence of a T residue at position 1021 and the presence of a T residue at position 1019. Both the 20n and 22n product were detected in roughly equal amounts indicating that the target nucleic acid was from an individual heterozygous for the G1012A mutation. If the patient was homozygous normal, then only a 22n product should be detected. If the patient was homozygous affected, then only the 20n product should be detected. The relative intensity of the 22n product to the 20n product allows one to determine the relative levels of the normal and mutant allele in a target nucleic acid sample. This is especially useful for analysing complex samples where there may be a large difference between the levels of a particular normal and mutant allele.

B) Redesign of the adjacent primer so that the 3' end of the primer was at position 1023, 1024 or 1025 and so that the primer maintained an appropriate optimal length (by adjusting the 5' endpoint appropriately) is permissible. For instance, if the adjacent primer is moved 3 nucleotides in the 5' direction, the primer sequence would be 5'CTG CAC GAA GCA CAG TGA CT 3'. Thus a product of 23n would be generated from the mutant allele and a product of 25n would be generated from the normal allele. There would not be any need to remove the non utilised primers since the adjacent primer would be 20n in length. This modification is depicted in FIG. 2.

EXAMPLE 2

In certain instances, it is advantageous to design the primers for amplification in accordance with the invention so that a greater and/or a clearer size difference exists between the glycosylase cleaved products diagnostic of the presence or absence of a particular sequence at a candidate locus. This can be achieved by altering the sequence of one or both of the primers so that the position of incorporation of the glycosylase recognisable substrate base(s) distal to the adjacent primer and the candidate locus is altered. This can be achieved by synthesising the primers so that some or all of the residues promoting incorporation of glycosylase substrate base(s) in the newly synthesised DNA are replaced by nucleotides which do not promote the incorporation of the glycosylase substrate base(s).

The protocol used in the present Example was exactly the same as that described in Example 1 except that the distal primer was synthesised with an inosine residue at the penultimate 3' position (position 1019) and exonuclease treatment was not carried out to remove the nonutilised primer as this was not necessary in this case. Thus, during amplification of the target strand a cytosine residue rather than an uracil residue was incorporated opposite position 1019 in the newly synthesised DNA. As a result, glycosylase mediated cleavage of the amplified products resulted in a 23n fragment arising from the mutant allele and a 28n fragment arising from the normal allele as shown in FIG. 3.

Greater differences may be achieved by preventing the incorporation of additional or all uracil residues at potential positions distal to the candidate locus to the extent where cleavage of the target strand only occurs at the candidate locus if an uracil residue is present at the locus. The same approach can also be used to prevent incorporation of additional or all uracil residues at potential positions opposite the adjacent primer on the complementary target strand.

EXAMPLE 3

Cleavage of the N-glycosidic bond between a base and the DNA backbone releases the base from the DNA and results in the generation of an apurinic or apyrimidinic site (AP site). The phosphodiester bond on the 3' side of the AP site is alkali labile and is also susceptible to cleavage at neutral pH by β-elimination. Thus, treatment of a DNA sample bearing an AP site with alkali or by heating causes cleavage of the phosphodiester bond of the DNA backbone and results in a DNA terminus with a 5' phosphate moiety and a terminus with a 3' deoxyribosephosphate, subsequent removal of the 3' terminal deoxyribosephosphate can be achieved by a variety of methods including treatment with the enzyme exonuclease III or endonuclease IV. It was observed that heating of amplified DNA fragments bearing one or more AP sites for 15 min. at 95° C. after uracil DNA-glycosylase cleavage resulted in cleavage of the AP site and generated products with and without a 3' terminal deoxyribosephosphate in about equal proportions. This differential cleavage may be exploited to facilitate accurate detection of the products of the glycosylase mediated cleavage process.

The protocol of Example 2 was repeated except that following uracil DNA-glycosylase treatment of the amplified target nucleic acid, the AP sites generated in the amplified product were cleaved by heating the mixture for 15 min. at 95° C. and because no NaOH was added, it was not necessary to neutralise the reaction. Following completion of the protocol as described in Example 1. analysis of the autoradiograph showed four cleavage products (a 28n product and a product about 1 nucleotide larger which is the 28n product plus 3'-terminal deoxyribosephosphate (28n+) and a 23n product and a product about 1 nucleotide larger which is the 23n product plus 3'-terminal deoxyribosephosphate (23n+)) in approximately equal amounts and the nonutilised labelled primer. This modification is depicted in FIG. 4.

The 23n and 23n+ products could only have been generated if an uracil residue was incorporated at position 1021 in the target strand. Thus the detection of a 23n and 23n+ fragment is diagnostic of the presence of a T residue at position 1021. In the normal allele the first uracil incorporated should be at position 1016 and should result in a 28n product. Thus the detection of a 28n and 28n+ product was diagnostic of the absence of a T residue at position 1021 and the presence of a T residue at position 1019. In this Example, both the 23n, 23n+, 28n, and 28n+ products were detected in roughly equal amounts indicating that the target nucleic acid was from an individual heterozygous for the G1021A mutation. This approach is especially useful for a multiplex approach since conditions can be readily designed where the appearance of fragments which are larger than the nonutilised primer by a single 3'-terminal deoxyribosephosphate are diagnostic of the presence or absence of a particular sequence at a candidate locus.

EXAMPLE 4

Glycosylase mediated cleavage of a particular sequence at a candidate locus in a target strand of a target nucleic acid sample also permits detection of cleavage products using solid phase or immobilised technology. This feature of the invention permits high throughput of samples and avoids the use of time consuming gel electrophoresis analysis. Any candidate locus may be investigated for the presence or absence of a particular sequence by this technology. The main areas for this application are in detection of gene mutations in a target sample and identification of specific organisms.

This Example and Examples 5 and 6 illustrate application in both areas as follows:

A procedure was used which was similar to that used in Example 1 in that the target nucleic acid was DNA extracted from a patient with malignant hyperthermia, the candidate locus was nucleotide 1021 in the human RYR1 gene and the objective was to determine if an A:T base pair was present at the candidate locus in one or both of the RYR1 alleles in the patient. The procedure is depicted in FIG. 5. In this case, the lower strand was the "target strand" and the upper strand was the "complementary strand". The presence or absence of a T(U) nucleotide at the candidate locus on the target strand was determined.

The adjacent and distal primers used were the same as those used in Example 1 except that the adjacent primer is biotinylated at the 5' end, and in the distal primer, all of the A residues were replaced by inosines. As a result of replacement of the A residues, the amplified target strand would only have contained a single uracil residue if an A:T base pair was present at the candidate locus. Thus cleavage of the target strand by uracil DNA-glycosylase mediated cleavage could only occur at a single position (1021) if a uracil residue was present. Therefore, cleavage of the amplified target strand in this instance is diagnostic of the presence of an A:T base pair at position 1021 in the target nucleic acid sample.

The adjacent primer was biotinylated at the 5' end during synthesis. The target nucleic acid sample was amplified by PCR as follows: the reaction mix for PCR contained 200 ng genomic DNA from the affected patient, 0.2 mM dCTP, dGTP, dATP and dUTP, 1 uCi alpha$^{32}$P dCTP (3000 Ci/mmol), 1.5 mM MgCl$_2$, 50 mM KCl, 10 mM Tris-HCl pH 9.0, 0.01 % Triton X-100. 6 pmoles of each primer in a total volume of 9 μl. The reaction mix was then overlaid with an equal volume of mineral oil and a hot start PCR was performed wherein the reaction mix was heated to 80° C. for 5 min prior to addition of 1 unit of Taq polymerase (bringing the total volume to 25 μl). 30 Cycles of 94° C. for 60 sec., 59° C. for 60 sec. and 72° C. for 60 sec. were carried out in a thermocycler.

Immobilisation of the product was carried out by adding 1 μl of the aqueous PCR reaction to a tube, labelled tube A, containing 20 μl streptavidin coated magnetic beads (Dynal beads, Dynal is a trade mark) and 19 μl sterile water and incubating at room temperature for 10 minutes. The tube was then placed in a magnetic stand which caused the beads with the attached biotin labelled PCR product to accumulate against one side of the tube. The supernatant containing unincorporated label and unused distal primer and nucleotide triphosphates was removed and the beads with trapped PCR amplified DNA were washed several times in buffer containing 10 mM Tris-HCl pH 7.5, 1 mM EDTA and 1 M NaCl. The amplified DNA was then denatured by adding 40 μl of 0.1 M NaOH. The complementary strand was removed in the supernatant and the target strand remained attached to the streptavidin coated magnetic beads. The beads were again washed with 40 μl of 0.1 M NaOH followed by a wash in the aforementioned buffer. The immobilised target strand was then treated with 0.05 units uracil DNA-glycosylase and cleaved at the AP-site by adding alkali to 0.25 M NaOH final concentration. The released material was then removed to another tube, labelled tube B, and monitored for the presence of $^{32}$P by scintillation counting. The tube containing the cleaved immobilised PCR product was also monitored for the presence of $^{32}$P.

Monitoring for the present of $^{32}$P by scintillation counting demonstrated that following uracil DNA-glycosylase cleavage, about half of the radioactive material was released to tube B. This demonstrated that about half of the immobilised PCR product was cleaved due to the presence of an U residue at the candidate locus. Thus it could be concluded that the target sample was heterozygous for the A:T base pair at position 1021 in the RYR1 gene.

EXAMPLE 5

Glycosylase mediated cleavage with immobilisation was used to detect the presence of pathogenic organisms of the *Mycobacteriun tuberculosis* complex.

The MPB70 gene is specifically found in *Mycobacterium tuberculosis* complex organisms and several reports have been published where detection of the MPB70 gene by PCR or other means can be used successfully to diagnose the presence of the complex. In this example, specific amplification of a section of the MPB70 gene was carried out so that a single U and label was incorporated in the PCR product. Thus, immobilisation of the product, followed by cleavage with uracil DNA-glycosylase should have released labelled product which could readily be detected.

As shown in FIG. 6, specific primers were designed to amplify a section of the MPB70 gene so that the amplified section of the target strand delineated by the primers contained several guanine, cytosine or adenine nucleotides and a single uracil residue. To achieve this, the distal primer was designed so that no uracils were incorporated opposite it on the target strand. Following amplification using an adjacent primer with a capture agent and a labelled nucleotide precursor, the amplified target strand was immobilised and cleaved with uracil DNA-glycosylase. Thus a labelled fragment of the target strand was released by this process and could be readily detected.

More specifically, the objective in this Example was to detect the presence of an amplified fragment of MPB70 (nucleotide 472–540) by monitoring the cleavage of an uracil residue at position 496, incorporated during extension of the adjacent primer. Primers were designed so that a GCA rich sequence (target strand) within the MPB70 gene was amplified using dGTP, dCTP, dUTP and dATP. The distal primer was designed so that inosines (or mismatches) were substituted for adenine residues thereby ensuring that the only uracil present in the target strand of the amplified product was at position 496. The adjacent primer was biotinylated at the 5' end. The sequence of the target nucleic acid at the candidate locus region and the sequence of both the adjacent primer and the distal primer are shown in FIG. 6.

The target nucleic acid sample was amplified by PCR as follows: the reaction mix for PCR contained 200 ng genomic DNA (or 1 $\mu$l of a 1/200 dilution of a PCR amplified region of the MPB70 gene). 0.2 mM dATP. dCTP, dGTP and dUTP, and 1 $\mu$Ci a$^{32}$P dCTP (3000/Ci/mmol), 1.5 mM MgCl$_2$, 50 mM KCl, 10 mM Tris-HCl pH 9.0, 0.1 % Triton X- 100, 6 pmoles of each primer in a total volume of 9 $\mu$l. The reaction mix was then overlaid with 20 $\mu$l of mineral oil and a hot start PCR was performed wherein the reaction mix was heated to 94° C. for 5 min prior to addition of 1 unit of Taq polymerase (bringing the total volume to 10 $\mu$l). 30 Cycles of 94° C. for 60 sec., 58° C. for 60 sec. and 72° C. for 60 sec. were carried out in a thermocycler followed by removal of the aqueous reaction mixture to a separate microtube.

Immobilisation of the product was carried out by adding 1 $\mu$l of the aqueous PCR reaction to a tube, labelled tube A, containing 20 $\mu$l streptavidin coated magnetic beads (Dynal beads) and 19 $\mu$l sterile water and incubating at room temperature of 10 min. The tube was then placed in a magnetic stand which caused the beads with the attached biotin labelled PCR product to accumulate against one side of the tube. The supernatant containing unincorporated label and unused distal primer and nucleotide triphosphates was removed and the beads with trapped PCR amplified DNA were washed several times in buffer containing 10 mM Tris-HCl pH 7.5, 1 mM EDTA and 1 M NaCi. The amplified DNA was then denatured by adding 40 $\mu$l of 0.1 M NaOH. The complementary strand was removed in the supernatant and the target strand remained attached to the streptavidin coated magnetic beads. The beads were again washed with 40 $\mu$l of 0.1 M NaOH followed by a wash in the aforementioned buffer. The immobilised target strand was then treated with 0.05 units uracil DNA-glycosylase and cleaved at the AP-site by adding alkali to 0.25 M NaOH final concentration. The released material was then removed to another tube, labelled tube B, and monitored for the presence of $^{32}$P by scintillation counting. The tube containing the cleaved immobilised PCR product is also monitored for the presence of $^{32}$P.

Monitoring for the presence of $^{32}$P by scintillation counting demonstrated that following uracil DNA-glycosylase cleavage, the radioactive material was released to tube B. This demonstrated that the immobilised PCR product was cleaved due to the presence of an U residue at the candidate locus. Thus it could be concluded that the target sample originated from *Mycobacterium tuberculosis* complex.

EXAMPLE 6

Figure 7:
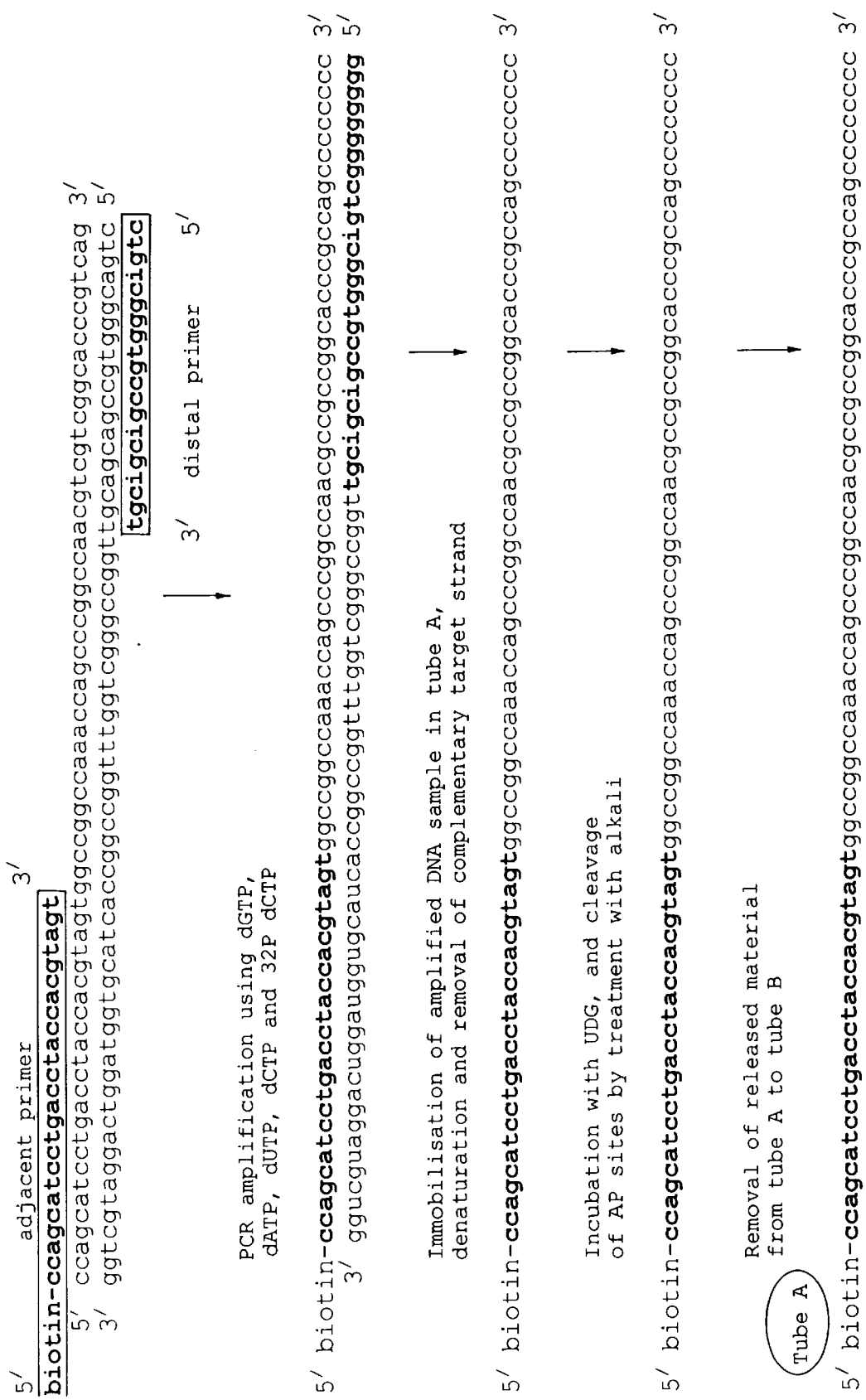
FIG. 7 is a schematic representation of the procedure described in Example 6.

The procedure of Example 5 was repeated except that the reaction was carried out using the adjacent primer designed in a different way. In this case, the adjacent primer was designed so that no uracils were incorporated into the target stand during amplification (shown in FIG. 7). Thus, in this case, the amplified product should have been resistant to cleavage with uracil DNA-glycosylase and so the label should not have been released to tube B. In this case, monitoring for the presence of $^{32}$P by scintillation counting demonstrated that the label in tube B remained immobilised after incubation with uracil DNA-glycosylase. No label was released to tube B. This application is especially useful for verifying that the correct DNA is immobilised since spurious PCR products generated would be expected to have uracil residues incorporated and thus, label should be released to tube B. The combination of Examples 5 and 6 allows the investigator to diagnose the presence or absence of *Mycobacterium tuberculosis* complex with a high degree of confidence.

EXAMPLE 7

Amplification of specific fragments of DNA of a specific size using preselected primers is commonly used for diagnostic purposes in the DNA diagnostics area. One of the limitations of such a diagnostic approach is that artefactual amplification products of the same size as the diagnostic product in question can arise and can potentially result in misdiagnosis. Thus, a method which increases the confidence limit or verifies that a diagnostic amplified fragment is correct has significant value in the diagnostic area since it improves the accuracy of diagnosis and is superior to diagnosis by amplification alone.

Amplification of specific fragments of the MPB70 gene found in *Mycobacterium tuberculosis* complex organisms using specific primers have been used to diagnose the presence of these organisms in samples. In this Example, the method according to the invention was used to check that a 116 bp and a 130 bp fragment of the MPB70 gene amplified from *Mycobacterium tuberculosis* complex using specific primers was correct. First of all, PCR was employed using specific primers and a *Mycobacterium tuberculosis* complex DNA sample so that a 116 bp and 130 bp product was amplified from the MPB70 gene. The primers and amplification conditions were designed so that when the 116 bp and 130 bp amplification products were cleaved with uracil DNA-glycosylase, fragments of a specific size should be generated verifying that the initial amplification products were correct.

The amplification strategy is shown in FIG. 8. As can be seen, primer A (5'ggcctcggtgcagggaatgtc3') and B (5'ccaggtttacttgcggattga3') were selected to amplify a 116 bp region of the MPB70 gene encompassing nucleotide 320 to nucleotide 436. The primers were also selected so that the first uracil incorporated was 11 nucleotides downstream of the 3' end of the primer A and 2 nucleotides downstream of primer B. Similarly, primer C and D were selected to amplify a 130 bp region of the MPB70 gene encompassing nucleotide 551 to nucleotide 681. The first uracil incorporated in this case was 26 nucleotides downstream of the 3' end of the primer C and 2 nucleotides downstream of primer D. Amplification of the 116 bp and 130 bp of the MPB70 gene using labelled primers, followed by cleavage with uracil-DNA-glycosylase should result in a 32n and a 23n fragment from the 116 bp PCR product and a 47n and a 23n fragment from the 130 bp PCR product.

The 116 bp product was amplified from a *Mycobacterium tuberculosis* complex DNA sample by PCR as follows. The reaction mix for PCR contained 200 ng *Mycobacterium tuberculosis* complex DNA. 0.2 mM dATP,dCTP, dGTP and dUTP, 1.5 mM $MgCl_2$, 50 mM KCl. 10 mM Tris-HCl pH 9.0, 0.1%Triton X-100 and 6 pmoles of primer A and primer B in a total volume of 19 µl. In the first amplification reaction mix, primer A was end-labelled using $\gamma^{32}$ ATP and polynucleotide kinase, while primer B was labelled in the second amplification. The reaction mixes were then overlaid with an equal volume of mineral oil and a hot start PCR was performed wherein the reaction mixes were heated to 94° C. for 5 min prior to addition of 1 unit of Taq polymerase (bringing the total volume to 20 µl). Thirty cycles of 94° C. for 60 sec., 57° C. for 60 sec. and and 72° C. for 60 sec. were carried out in a thermocycler followed by removal of the aqueous reaction mixes to separate microtubes. The reaction mixes bearing the amplified target nucleic acids were then treated with exonuclease I to digest the primers not extended in the amplification step. This was achieved by incubating 3 µl of the PCR reaction mixes with 0.5 units of exonuclease I at 37° C. for 30 min. The exonuclease was subsequently heat inactivated by incubating the reaction at 80° C. for 15 min.

Uracil DNA glycosylase (0.05 units) was then added to 3 µl of the above reaction mixes and incubated at 37° C. for 30 min. Following Uracil DNA glycosylase treatment, the apyrimidinic sites generated in the amplified products were cleaved to completion by adding NaOH to a final concentration of 0.05 M and heating the mixtures for 15 min at 95° C. The reaction mixes were then neutralised by addition of Tris base to 0.03 M final concentration. An equal volume of formamide loading dye (90% formamide, 0.025% Bromophenol blue, 0.025% Xylene cylanol) was added to the mixes which were then heated to 85° C. for 5 min. 5 µl of each mix was then loaded onto a 20% denaturing (7 M urea) polyacrylamide gel and electrophoresis was carried out for 3 hours at 400 volts for size analysis of the cleaved products in the sample. Following electrophoresis, autoradiography was carried out by exposing the gel directly to X-ray photographic film for 12 hours at −70° C.

Analysis of the autoradiographed products showed the following cleavage pattern. In the first reaction where primer A was end- labelled, a product of 32n was observed. The 32n product could only have been generated if an uracil residue was incorporated 12 nucleotides downstream of the 3' end of the primer A. In the second reaction where primer B was end-labelled, a product of 23n was observed. The 23n product could only have been generated if an uracil residue was incorporated 3 nucleotides downstream of the 3' end of primer B.

The 130 bp product was amplified from a *Mycobacterium tuberculosis* complex DNA sample by PCR exactly as outlined above except that primer C (5'catcctgacctaccacgtagt3') and primer D (5'gtcggcgttaccgaccttgag3') were used in place of primer A and primer B. Analysis of the autoradiographed products showed the following cleavage pattern. In the reaction where primer C was end-labelled, a product of 47n was observed. The 47n product could only have been generated if an uracil residue was incorporated 27 nucleotides downstream of the 3' end of primer A. In the reaction where primer D was end-labelled, a product of 23n was observed. The 23n product could only have been generated if an uracil residue was incorporated 3 nucleotides downstream of the 3' end of primer D.

The amplification process described here can be performed independently with separately labelled primers as described or as a multiplex reaction where all four labelled primers are included in a single amplification reaction. In the latter case., labelled products of 47n, 32n and 23n are detectable in a single lane following cleavage with uracil-DNA-glycosylase, electrophoresis and autoradiography.

The probability or an uracil being present at a particular location in a DNA fragment is ¼ or 0.25. The probability of an uracil not being present at a location is ¾ or 0.75. In the case of primer A, it was extended 11 nucleotides before it was cut. The probability of such an extension occurring randomly is $0.75^{11}=0.042$. The extended primer cut at the 12 nucleotide incorporated showing that an uracil was present at this location. The probability of the uracil occurring at that particular position was 0.25. Thus overall, the probability of an eleven base pair extension product occurring randomly would be 0.042×0.25=0.0105. Similarly, the probability of primer B extending by two bases would be 0.752×0.25= 0.14. Overall, the probability of a random 116 bp product cleaving to a 32n (11 nucleotide extension of the 21n primer A) and a 23n (2 nucleotide extension of the 21n primer B) product would be 0.0105×0.14=0.0014. Similar calculations performed for the 130 bp product where primer C and D are extended by 26n and 2n respectively show that the probability of such extension products arising randomly is 0.000019. Taking both PCR products together, the probability of the observed products occurring randomly is 0.000000027. Thus, this Example demonstrates the application of the method according to the invention in the verification of PCR products from *Mycobacterium tuberculosis*. Thus the application of the method according to the invention in this manner offers a rapid and accurate means for verification of amplified nucleic acids from diagnostic or other purposes.

EXAMPLE 8

The fact that Uracil-DNA-glycosylase is active on both single stranded and double stranded DNA allows the use of this enzyme in the analysis of linear amplification products bearing uracils residues.

Linear amplification of single stranded DNA can offer significant advantages over exponential DNA amplification in several instances. However, linear amplification suffers from some drawbacks since single stranded DNA generated by linear amplification is generally less amenable to rapid analysis by comparison with double stranded DNA. For example, single stranded DNA is generally not cleaved by restriction enzymes. Furthermore, exponential amplification of genomic DNA using a specific pair of primers in PCR results in the production of a double stranded DNA product of a specific size facilitating analysis by sizing technology. The 5' and 3' ends of the fragment are defined by the forward and reverse primer. By contrast linear amplification of genomic DNA produces fragments with defined 5' ends but with undefined 3' ends. In this Example, we demonstrate the use of the method according to the invention to generate single stranded fragments of a specific size following linear amplification. Amplification of a nucleic acid fragment bearing a candidate locus is usually required to determine if a particular sequence is present or absent at the candidate locus. Often it is necessary or desirable to examine multiple candidate loci in amplified DNA for the presence of particular sequences. This is especially desirable for detection of mutations in genes causing human disease. Thus, any method allowing simultaneous amplification of multiple candidate loci followed by simultaneous analysis of the candidate loci is advantageous by comparison with single locus analysis. Amplification of a nucleic acid fragment(s) bearing multiple candidate loci can be achieved by linear amplification or exponential amplification methods. However, the analysis of the multiple loci is often rate limiting requiring several independent approaches or full scale DNA sequencing. In this Example we also demonstrate the application of the method to simultaneously determine if particular mutations are present or absent at two specific candidate loci.

Figure 9:
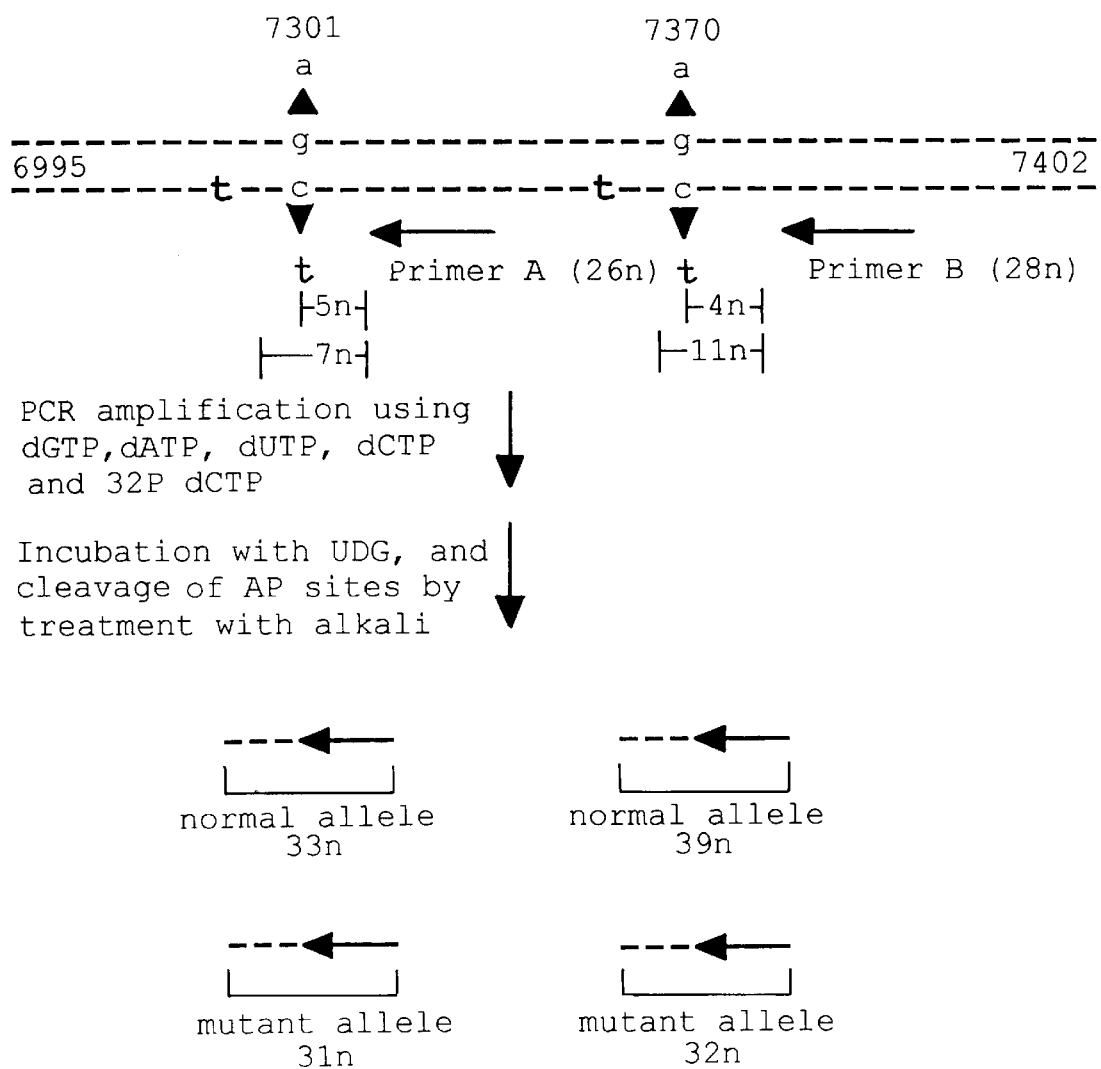
FIG. 9 is a schematic representation of the procedure described in Example 8.

The method according to the invention was used to simultaneously detect the presence or absence of a G to A base substitution mutation causal of malignant hyperthermia at the candidate loci 7301 and 7370 in the human skeletal ryanodine receptor gene (RYR1) in two patients heterozygous for either mutation. The sequence of steps is illustrated in FIG. 9. In this case, the target nucleic acid was a DNA fragment amplified by PCR from skeletal muscle cDNA from two patients (A and B) with malignant hyperthermia. The lower strand shown in FIG. 9 is the target strand. Primer A (26n, 5'ggcttggattagatgcatctctggtg3') was designed so that the first uracil incorporated into the extended primer in a linear amplification of the target DNA would be positioned at the sixth nucleotide incorporated in the case of the mutant allele and at the eighth nucleotide in the case of the normal allele. Primer B (28n, 5'gaattccaaggtcctccaagggcacaag3') was designed so that the first uracil incorporated would be positioned at the fifth nucleotide incorporated in the case of the mutant allele and at the twelfth nucleotide in the case of the normal allele. Both primers were extended in the same direction by linear amplification. The presence or absence of a T(U) at the candidate loci was determined by cleavage with uracil-DNA-glycosylase, gel electrophoresis and autoradiography. The target nucleic acid can be genomic DNA or any amplified section of DNA. In this Example, the target nucleic acid was generated by amplifying the 6995 to 7402 region of the RYR1 gene from cDNA using PCR.

Primers A and B were end-labelled with $\gamma^{32}P$ as described in Example 1. The target nucleic acid from patient A and patient B was treated with an equal volume of exonuclease 1 (0.5 units/$\mu$l) at 37° C. for min to degrade primers not utilised in the PCR. The exonuclease was subsequently inactivated by incubation at 80° C. for 15 min. This treatment was necessary to prevent any exponential amplification in subsequent steps. This step is not necessary when genomic DNA is the target nucleic acid. 1 $\mu$l of the target nucleic acid samples were incubated independently with 6 pmol of labelled primer A and labelled primer B, 0.2 mM dATP, dCTP, dGTP and dUTP, 2 mM $MgSO_4$, 10 mM KCl, 20 mM Tris-HCl pH 8.8, 10 mM$(NH_4)_2$ $SO_4$, 0.1% Triton X-100 in a total volume of 19 $\mu$l. The reaction mixes were then overlaid with an equal volume of mineral oil and a hot start to the linear amplification process was performed wherein the reaction mix was heated to 94° C. for 5 min prior to addition of 0.5 units of Vent DNA Polymerase (exo) (bringing the total volume to 20 $\mu$l). Thirty cycles of 94° C. for 60 sec., 55° C. for 60 sec. and 72° C. for 60 sec. were carried out in a thermocycler followed by removal of the aqueous reaction mixture to a separate microtube.

Uracil-DNA-glycosylase (0.05 units) was then added to 5 $\mu$l of the above reactions and incubated at 37° C. for 30 min. Following uracil-DNA-glycosylase treatment, the apyrimidinic sites generated in the amplified product were cleaved to completion by adding NaOH to a final concentration of 0.05 M and heating the mixtures for 15 min at 95° C. The reactions were then neutralised by addition of Tris base to 0.03 M final concentration. An equal volume of formamide loading dye (90% formamide. 0.025% bromophenol blue. 0.025% xylene cylanol) was added to the samples which were then heated to 85° C. for 5 min. 5 $\mu$l of the samples were then loaded onto a 20% denaturing (7 M urea) polyacrylamide gel and electrophoresis was carried out for 3 hours at 400 volts for size analysis of the cleaved products in the sample. Following electrophoresis, autoradiography was carried out by exposing the gel directly to X-ray photographic film for 12 hours at −70° C.

Analysis of the sample from patient A showed cleavage products of 39n, 33n and 31n in addition to the 26n and 28n non utilised primers. This pattern of cleavage products could only be produced if patient A was homozygous for the normal allele of the RYR1 gene at candidate locus 7370 and heterozygous for the G7301 A mutation. Analysis of the sample from patient B showed cleavage products of 39n, 33n and 32n in addition to the 26n and 28n non utilised primers. This pattern of cleavage products could only be produced if patient B was homozygous for the normal allele of the RYR I gene at candidate locus 7301 and heterozygous for the G7370A mutation. Thus, the application of the method according to the invention has permitted simultaneous analysis of two candidate loci for the presence or absence of specific mutations. In this Example, two candidate loci have been investigated. The method can readily be applied to multiple candidate loci in genomic or amplified target DNA as long as the primers chosen support linear amplification but do not permit exponential amplification.

Generation of amplified nucleic acid fragments of specific size is regularly used in diagnosis of infectious agents and in the verification of amplified nucleic acid molecules. In this Example, the use of the method according to the invention generated single stranded fragments of a specific size following linear amplification. This is a useful application of the method since it permits the use of linear amplification rather than exponential amplification to generate amplified fragments of a specific size.

We claim:

1. A method for rapidly detecting the presence or absence of a particular nucleic acid sequence at a candidate locus in a target nucleic acid sample which comprises the steps of:
   i) introducing a modified base which is a substrate for a DNA glycosylase into said candidate locus at one or more preselected positions;
   ii) excising the modified base by means of said DNA glycosylase so as to generate an abasic site;
   iii) cleaving phosphate linkages at abasic sites generated in step ii); and
   iv) analysing the cleavage products of step iii) so as to identify in said target nucleic acid sequence the presence or absence of said particular nucleic acid sequence at said candidate locus.

2. A method according to claim 1, wherein the candidate locus is amplified using a combination of normal DNA precursor nucleotides and at least one modified precursor nucleotide.

3. A method according to claim 2, wherein at least one of the primers for the amplification is positioned adjacent to the candidate locus.

4. A method according to claim 3, wherein the at least one primer is labelled.

5. A method according to any one of claims 2–4, wherein at least one of the precursor nucleotide(s) is labelled.

6. A method according to claim 1 wherein the modified base is introduced by chemical modification of an existing base at the candidate locus.

7. A method according to claim 1 wherein the modified base is excised by means of a DNA glycosylase enzyme.

8. A method according to claim 7, wherein the DNA-glycosylase enzyme is uracil DNA-glycosylase.

9. A method according to claim 7 or 8, wherein the substrate for the DNA glycosylase enzyme is immobilised.

10. A method according to claim 1 wherein the phosphate linkages at the abasic sites are cleaved by treatment with alkali.

11. A method according to claim 1 wherein the phosphate linkages at the abasic sites are cleaved by a heat treatment.

12. A method according to claim 1 wherein the phosphate linkages at the abasic sites are cleaved by treatment with an enzyme.

13. A method according to claim 12, wherein the enzyme is an enzyme which cleaves specifically at apurinic or apyrimidinic sites.

14. A method according to claim 1 wherein the modified base is uracil or hypoxanthine.

15. A method according to claim 1 wherein the target nucleic acid sample is DNA.

16. A method according to claim 15, wherein the DNA is single stranded, homoduplex or heteroduplex DNA.

17. A method according to claim 1 wherein the target nucleic acid sample is RNA.

18. A method according to claim 17, wherein the target nucleic acid sample is RNA, wherein the RNA is converted into a cDNA by reverse transcription prior to the amplification step.

19. A method according to claim 1, wherein the cleavage products are detected by hybridisation with specific nucleic acid probes.

20. A test kit or pack for carrying out a method according to claim 1.

* * * * *

SEQUENCE LISTING (1) GENERAL INFORMATION:

(iii) NUMBER OF SEQUENCES: 69

(2) INFORMATION FOR SEQ ID NO: 1:

(i) SEQUENCE CHARACTERISTICS:
      (A) LENGTH: 20 base pairs
      (B) TYPE: nucleic acid
      (C) STRANDEDNESS: double (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO: 1:

CTGCACGAAG CACAGTGACT                                           20

(2) INFORMATION FOR SEQ ID NO: 2:

(i) SEQUENCE CHARACTERISTICS:
        (A) LENGTH: 21 base pairs
        (B) TYPE: nucleic acid
        (C) STRANDEDNESS: double
        (D) TOPOLOGY: circular (ii) MOLECULE TYPE: DNA (genomic)

(iii) HYPOTHETICAL: NO (iv) ANTI-SENSE: NO (vi) ORIGINAL SOURCE:
        (A) ORGANISM: Mycobacterium tuberculosis (xi) SEQUENCE DESCRIPTION: SEQ ID NO: 2:

GGCCTCGGTG CAGGGAATGT C                                         21

(2) INFORMATION FOR SEQ ID NO: 3:

(i) SEQUENCE CHARACTERISTICS:
        (A) LENGTH: 21 base pairs
        (B) TYPE: nucleic acid
        (C) STRANDEDNESS: double
        (D) TOPOLOGY: circular (ii) MOLECULE TYPE: DNA (genomic)

(iii) HYPOTHETICAL: NO (iv) ANTI-SENSE: YES (vi) ORIGINAL SOURCE:
        (A) ORGANISM: Mycobacterium tuberculosis (xi) SEQUENCE DESCRIPTION: SEQ ID NO: 3:

CCAGGTTTAC TTGCGGATTG A                                         21

(2) INFORMATION FOR SEQ ID NO: 4:

(i) SEQUENCE CHARACTERISTICS:
        (A) LENGTH: 21 base pairs
        (B) TYPE: nucleic acid
        (C) STRANDEDNESS: double
        (D) TOPOLOGY: circular (ii) MOLECULE TYPE: DNA (genomic)

(iii) HYPOTHETICAL: NO (iv) ANTI-SENSE: NO (vi) ORIGINAL SOURCE:
        (A) ORGANISM: Mycobacterium tuberculosis (xi) SEQUENCE DESCRIPTION: SEQ ID NO: 4:

CATCCTGACC TACCACGTAG T                                         21

(2) INFORMATION FOR SEQ ID NO: 5:

(i) SEQUENCE CHARACTERISTICS:
        (A) LENGTH: 21 base pairs
        (B) TYPE: nucleic acid
        (C) STRANDEDNESS: double
        (D) TOPOLOGY: circular (ii) MOLECULE TYPE: DNA (genomic)

(iii) HYPOTHETICAL: NO (iv) ANTI-SENSE: YES (vi) ORIGINAL SOURCE:
        (A) ORGANISM: Mycobacterium tuberculosis (xi) SEQUENCE DESCRIPTION: SEQ ID NO: 5:

```
GTCGGCGTTA CCGACCTTGA G                                         21
```

(2) INFORMATION FOR SEQ ID NO: 6:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: YES (vi) ORIGINAL SOURCE:
        (A) ORGANISM: Homo sapiens (xi) SEQUENCE DESCRIPTION: SEQ ID NO: 6:

```
GGCTTGGATT AGATGCATCT CTGGTG                                    26
```

(2) INFORMATION FOR SEQ ID NO: 7:

(i) SEQUENCE CHARACTERISTICS:
        (A) LENGTH: 28 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: YES (vi) ORIGINAL SOURCE:
        (A) ORGANISM: Homo sapiens (xi) SEQUENCE DESCRIPTION: SEQ ID NO: 7:

```
GAATTCCAAG GTCCTCCAAG GGCACAAG                                  28
```

(2) INFORMATION FOR SEQ ID NO: 8:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
    (A) ORGANISM: Homo sapiens (xi) SEQUENCE DESCRIPTION: SEQ ID NO: 8:

GCCCCCCTGA GATCAAGTAC                                           20

(2) INFORMATION FOR SEQ ID NO: 9:

(i) SEQUENCE CHARACTERISTICS:
        (A) LENGTH: 41 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO: 9:

GCCCCCCTGA GATCAAGTAC AGGGAGTCAC TGTGCTTCGT G                    41

(2) INFORMATION FOR SEQ ID NO: 10:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: YES (vi) ORIGINAL SOURCE:
        (A) ORGANISM: Homo sapiens (xi) SEQUENCE DESCRIPTION: SEQ ID NO: 10:

CACGAAGCAC AGTGACTCCC                                           20

(2) INFORMATION FOR SEQ ID NO: 11:

(i) SEQUENCE CHARACTERISTICS:
        (A) LENGTH: 41 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO: 11:

GCCCCCCTGA GATCAAGTAC GGGGAGUCAC UGUGCUUCGU G                    41

(2) INFORMATION FOR SEQ ID NO: 12:

(i) SEQUENCE CHARACTERISTICS:
        (A) LENGTH: 41 base pairs

```
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: YES (vi) ORIGINAL SOURCE:
        (A) ORGANISM: Homo sapiens (xi) SEQUENCE DESCRIPTION: SEQ ID NO: 12:

CACGAAGCAC AGTGACTCCC CGUACUUGAU CUCAGGGGGG C                     41

(2) INFORMATION FOR SEQ ID NO: 13:

(i) SEQUENCE CHARACTERISTICS:
        (A) LENGTH: 41 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (ix) FEATURE:
        (A) NAME/KEY: misc_feature
        (B) LOCATION: 27
        (D) OTHER INFORMATION: N is a purine or a pyrimidine (ix) FEATURE:
        (A) NAME/KEY: misc_feature
        (B) LOCATION: 31
        (D) OTHER INFORMATION: N is a purine or a pyrimidine (ix) FEATURE:
        (A) NAME/KEY: misc_feature
        (B) LOCATION: 33
        (D) OTHER INFORMATION: N is a purine or a pyrimidine (ix) FEATURE:
        (A) NAME/KEY: misc_feature
        (B) LOCATION: 36..37
        (D) OTHER INFORMATION: N is a purine or a pyrimidine (ix) FEATURE:
        (A) NAME/KEY: misc_feature
        (B) LOCATION: 40
        (D) OTHER INFORMATION: N is a purine or a pyrimidine (xi) SEQUENCE DESCRIPTION: SEQ ID NO: 13:

GCCCCCCTGA GATCAAGTAC GGGGAGNCAC NGNGCNNCGN G                     41

(2) INFORMATION FOR SEQ ID NO: 14:

(i) SEQUENCE CHARACTERISTICS:
        (A) LENGTH: 41 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: YES (vi) ORIGINAL SOURCE:
```

(A) ORGANISM: Homo sapiens (ix) FEATURE:
         (A) NAME/KEY: misc_feature
         (B) LOCATION: 23
         (D) OTHER INFORMATION: N is a purine or apyrimipdine (ix) FEATURE:
         (A) NAME/KEY: misc_feature
         (B) LOCATION: 26
         (D) OTHER INFORMATION: N is a purine or a pyrimidine (ix) FEATURE:
         (A) NAME/KEY: misc_feature
         (B) LOCATION: 27
         (D) OTHER INFORMATION: N is a purine or a pyrimidine (ix) FEATURE:
         (A) NAME/KEY: misc_feature
         (B) LOCATION: 29
         (D) OTHER INFORMATION: N is a purine or
             a pyrimidine"

(ix) FEATURE:
         (A) NAME/KEY: misc_feature
         (B) LOCATION: 31
         (D) OTHER INFORMATION: N is a purine or
             a pyrimidine"

(xi) SEQUENCE DESCRIPTION: SEQ ID NO: 14:

CACGAAGCAC AGTGACTCCC CGNACNNGAN CNCAGGGGGG C                               41

(2) INFORMATION FOR SEQ ID NO: 15:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: Homo sapiens (xi) SEQUENCE DESCRIPTION: SEQ ID NO: 15:

GCCCCCCTGA GATCAAGTAC GGGGAG                                                26

(2) INFORMATION FOR SEQ ID NO: 16:

(i) SEQUENCE CHARACTERISTICS:
        (A) LENGTH: 22 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: YES (vi) ORIGINAL SOURCE:
         (A) ORGANISM: Homo sapiens (xi) SEQUENCE DESCRIPTION: SEQ ID NO: 16:

CACGAAGCAC AGTGACTCCC CG                                                    22

(2) INFORMATION FOR SEQ ID NO: 17:

```
    (i) SEQUENCE CHARACTERISTICS:
        (A) LENGTH: 41 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO: 17:

GCCCCCCTGA GATCAAGTAC AGGGAGTCAC TGTGCTTCGT G                        41

(2) INFORMATION FOR SEQ ID NO: 18:

(i) SEQUENCE CHARACTERISTICS:
        (A) LENGTH: 41 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO: 18:

GCCCCCCTGA GATCAAGTAC AGGGAGUCAC UGUGCUUCGU G                        41

(2) INFORMATION FOR SEQ ID NO: 19:

(i) SEQUENCE CHARACTERISTICS:
        (A) LENGTH: 41 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: YES (vi) ORIGINAL SOURCE:
        (A) ORGANISM: Homo sapiens (xi) SEQUENCE DESCRIPTION: SEQ ID NO: 19:

CACGAAGCAC AGTGACTCCC UGUACUUGAU CUCAGGGGGG C                        41

(2) INFORMATION FOR SEQ ID NO: 20:

(i) SEQUENCE CHARACTERISTICS:
        (A) LENGTH: 41 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens
```

(ix) FEATURE:
              (A) NAME/KEY: misc_feature
              (B) LOCATION: 27
              (D) OTHER INFORMATION: N is a purine or a pyrimidine (ix) FEATURE:
              (A) NAME/KEY: misc_feature
              (B) LOCATION: 31
              (D) OTHER INFORMATION: N is a purine or a pyrimidine (ix) FEATURE:
              (A) NAME/KEY: misc_feature
              (B) LOCATION: 33
              (D) OTHER INFORMATION: N is a purine or a pyrimidine (ix) FEATURE:
              (A) NAME/KEY: misc_feature
              (B) LOCATION: 36..37
              (D) OTHER INFORMATION: N is a purine or a pyrimidine (ix) FEATURE:
              (A) NAME/KEY: misc_feature
              (B) LOCATION: 40
              (D) OTHER INFORMATION: N is a purine or a pyrimidine (xi) SEQUENCE DESCRIPTION: SEQ ID NO: 20:

GCCCCCCTGA GATCAAGTAC AGGGAGNCAC NGNGCNNCGN G         41

(2) INFORMATION FOR SEQ ID NO: 21:

(i) SEQUENCE CHARACTERISTICS:
            (A) LENGTH: 41 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: YES (vi) ORIGINAL SOURCE:
            (A) ORGANISM: Homo sapiens (ix) FEATURE:
            (A) NAME/KEY: misc_feature
            (B) LOCATION: 21
            (D) OTHER INFORMATION: N is a purine or a pyrimidine (ix) FEATURE:
            (A) NAME/KEY: misc_feature
            (B) LOCATION: 23
            (D) OTHER INFORMATION: N is a purine or a pyrimidine (ix) FEATURE:
            (A) NAME/KEY: misc_feature
            (B) LOCATION: 26..27
            (D) OTHER INFORMATION: N is a purine or a pyrimidine (ix) FEATURE:
            (A) NAME/KEY: misc_feature
            (B) LOCATION: 30
            (D) OTHER INFORMATION: N is a purine or a pyrimidine (ix) FEATURE:
            (A) NAME/KEY: misc_feature
            (B) LOCATION: 32
            (D) OTHER INFORMATION: N is a purine or a pyrimidine (xi) SEQUENCE DESCRIPTION: SEQ ID NO: 21:

CACGAAGCAC AGTGACTCCC NGNACNNGAN CNCAGGGGGG C         41

(2) INFORMATION FOR SEQ ID NO: 22:

```
    (i) SEQUENCE CHARACTERISTICS:
        (A) LENGTH: 26 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO: 22:

GCCCCCCTGA GATCAAGTAC AGGGAG                                             26

(2) INFORMATION FOR SEQ ID NO: 23:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: YES (vi) ORIGINAL SOURCE:
        (A) ORGANISM: Homo sapiens (xi) SEQUENCE DESCRIPTION: SEQ ID NO: 23:

CACGAAGCAC AGTGACTCCC                                                    20

(2) INFORMATION FOR SEQ ID NO: 24:

(i) SEQUENCE CHARACTERISTICS:
        (A) LENGTH: 44 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO: 24:

GCCCCCCTGA GATCAAGTAC GGGGAGTCAC TGTGCTTCGT GCAG                          44

(2) INFORMATION FOR SEQ ID NO: 25:

(i) SEQUENCE CHARACTERISTICS:
        (A) LENGTH: 44 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens
```

(xi) SEQUENCE DESCRIPTION: SEQ ID NO: 25:

GCCCCCCTGA GATCAAGTAC GGGGAGUCAC UGUGCUUCGU GCAG                44

(2) INFORMATION FOR SEQ ID NO: 26:

(i) SEQUENCE CHARACTERISTICS:
        (A) LENGTH: 44 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: YES (vi) ORIGINAL SOURCE:
        (A) ORGANISM: Homo sapiens (xi) SEQUENCE DESCRIPTION: SEQ ID NO: 26:

CTGCACGAAG CACAGTGACT CCCCGUACUU GAUCUCAGGG GGGC                44

(2) INFORMATION FOR SEQ ID NO: 27:

(i) SEQUENCE CHARACTERISTICS:
        (A) LENGTH: 44 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (ix) FEATURE:
        (A) NAME/KEY: misc_feature
        (B) LOCATION: 27
        (D) OTHER INFORMATION: N is a purine or a pyrimidine (ix) FEATURE:
        (A) NAME/KEY: misc_feature
        (B) LOCATION: 31
        (D) OTHER INFORMATION: N is a purine or a pyrimidine (ix) FEATURE:
        (A) NAME/KEY: misc_feature
        (B) LOCATION: 33
        (D) OTHER INFORMATION: N is a purine or a pyrimidine (ix) FEATURE:
        (A) NAME/KEY: misc_feature
        (B) LOCATION: 36..37
        (D) OTHER INFORMATION: N is a purine or a pyrimidine (ix) FEATURE:
        (A) NAME/KEY: misc_feature
        (B) LOCATION: 40
        (D) OTHER INFORMATION: N is a purine or a pyrimidine (xi) SEQUENCE DESCRIPTION: SEQ ID NO: 27:

GCCCCCCTGA GATCAAGTAC GGGGAGNCAC NGNGCNNCGN GCAG                44

(2) INFORMATION FOR SEQ ID NO: 28:

(i) SEQUENCE CHARACTERISTICS:
        (A) LENGTH: 44 base pairs
        (B) TYPE: nucleic acid (C) STRANDEDNESS: double
            (D) TOPOLOGY: linear (ii) MOLECULE TYPE: DNA (genomic)

(iii) HYPOTHETICAL: NO (iv) ANTI-SENSE: YES (vi) ORIGINAL SOURCE:
            (A) ORGANISM: Homo sapiens (ix) FEATURE:
            (A) NAME/KEY: misc_feature
            (B) LOCATION: 26
            (D) OTHER INFORMATION: N is a purine or a pyrimidine (ix) FEATURE:
            (A) NAME/KEY: misc_feature
            (B) LOCATION: 29..30
            (D) OTHER INFORMATION: N is a purine or a pyrimidine (ix) FEATURE:
            (A) NAME/KEY: misc_feature
            (B) LOCATION: 33
            (D) OTHER INFORMATION: N is a purine or a pyrimidine (ix) FEATURE:
            (A) NAME/KEY: misc_feature
            (B) LOCATION: 35
            (D) OTHER INFORMATION: N is a purine or a pyrimidine (xi) SEQUENCE DESCRIPTION: SEQ ID NO: 28:

CTGCACGAAG CACAGTGACT CCCCGNACNN GANCNCAGGG GGGC         44

(2) INFORMATION FOR SEQ ID NO: 29:

(i) SEQUENCE CHARACTERISTICS:
            (A) LENGTH: 25 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: YES (vi) ORIGINAL SOURCE:
            (A) ORGANISM: Homo sapiens (xi) SEQUENCE DESCRIPTION: SEQ ID NO: 29:

CTGCACGAAG CACAGTGACT CCCCG         25

(2) INFORMATION FOR SEQ ID NO: 30:

(i) SEQUENCE CHARACTERISTICS:
            (A) LENGTH: 44 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Homo sapiens (xi) SEQUENCE DESCRIPTION: SEQ ID NO: 30:

GCCCCCCTGA GATCAAGTAC AGGGAGTCAC TGTGCTTCGT GCAG         44

(2) INFORMATION FOR SEQ ID NO: 31:

(i) SEQUENCE CHARACTERISTICS:
        (A) LENGTH: 44 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO: 31:

GCCCCCCTGA GATCAAGTAC AGGGAGUCAC UGUGCUUCGU GCAG                44

(2) INFORMATION FOR SEQ ID NO: 32:

(i) SEQUENCE CHARACTERISTICS:
        (A) LENGTH: 44 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: YES (vi) ORIGINAL SOURCE:
        (A) ORGANISM: Homo sapiens (xi) SEQUENCE DESCRIPTION: SEQ ID NO: 32:

CTGCACGAAG CACAGTGACT CCCUGUACUU GAUCUCAGGG GGGC                44

(2) INFORMATION FOR SEQ ID NO: 33:

(i) SEQUENCE CHARACTERISTICS:
        (A) LENGTH: 44 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (ix) FEATURE:
        (A) NAME/KEY: misc_feature
        (B) LOCATION: 27
        (D) OTHER INFORMATION: N is a purine or a pyrimidine (ix) FEATURE:
        (A) NAME/KEY: misc_feature
        (B) LOCATION: 31
        (D) OTHER INFORMATION: N is a purine or a pyrimidine (ix) FEATURE:
        (A) NAME/KEY: misc_feature
        (B) LOCATION: 33
        (D) OTHER INFORMATION: N is a purine or a pyrimidine (ix) FEATURE:
        (A) NAME/KEY: misc_feature
        (B) LOCATION: 36..37

(D) OTHER INFORMATION: N is a purine or a pyrimidine (ix) FEATURE:
         (A) NAME/KEY: misc_feature
         (B) LOCATION: 40
         (D) OTHER INFORMATION: N is a purine or a pyrimidine (xi) SEQUENCE DESCRIPTION: SEQ ID NO: 33:

GCCCCCCTGA GATCAAGTAC AGGGAGNCAC NGNGCNNCGN GCAG                    44

(2) INFORMATION FOR SEQ ID NO: 34:

(i) SEQUENCE CHARACTERISTICS:
         (A) LENGTH: 44 base pairs
         (B) TYPE: nucleic acid
         (C) STRANDEDNESS: double
         (D) TOPOLOGY: linear (ii) MOLECULE TYPE: DNA (genomic)

(iii) HYPOTHETICAL: NO (iv) ANTI-SENSE: YES (vi) ORIGINAL SOURCE:
         (A) ORGANISM: Homo sapiens (ix) FEATURE:
         (A) NAME/KEY: misc_feature
         (B) LOCATION: 24
         (D) OTHER INFORMATION: N is a purine or a pyrimidine (ix) FEATURE:
         (A) NAME/KEY: misc_feature
         (B) LOCATION: 26
         (D) OTHER INFORMATION: N is a purine or a pyrimidine (ix) FEATURE:
         (A) NAME/KEY: misc_feature
         (B) LOCATION: 29..30
         (D) OTHER INFORMATION: N is a purine or a pyrimidine (ix) FEATURE:
         (A) NAME/KEY: misc_feature
         (B) LOCATION: 33
         (D) OTHER INFORMATION: N is a purine or a pyrimidine (ix) FEATURE:
         (A) NAME/KEY: misc_feature
         (B) LOCATION: 35
         (D) OTHER INFORMATION: N is a purine or a pyrimidine (xi) SEQUENCE DESCRIPTION: SEQ ID NO: 34:

CTGCACGAAG CACAGTGACT CCCNGNACNN GANCNCAGGG GGGC                    44

(2) INFORMATION FOR SEQ ID NO: 35:

(i) SEQUENCE CHARACTERISTICS:
         (A) LENGTH: 23 base pairs
         (B) TYPE: nucleic acid
         (C) STRANDEDNESS: double
         (D) TOPOLOGY: linear (ii) MOLECULE TYPE: DNA (genomic)

(iii) HYPOTHETICAL: NO (iv) ANTI-SENSE: YES (vi) ORIGINAL SOURCE:
         (A) ORGANISM: Homo sapiens (xi) SEQUENCE DESCRIPTION: SEQ ID NO: 35:

CTGCACGAAG CACAGTGACT CCC                                           23

(2) INFORMATION FOR SEQ ID NO: 36:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (ix) FEATURE:
        (A) NAME/KEY: modified_base
        (B) LOCATION: 19
        (D) OTHER INFORMATION: /mod_base= i (xi) SEQUENCE DESCRIPTION: SEQ ID NO: 36:

GCCCCCCTGA GATCAAGTNC                                    20

(2) INFORMATION FOR SEQ ID NO: 37:

(i) SEQUENCE CHARACTERISTICS:
        (A) LENGTH: 44 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (ix) FEATURE:
        (A) NAME/KEY: modified_base
        (B) LOCATION: 19
        (D) OTHER INFORMATION: /mod_base= i (xi) SEQUENCE DESCRIPTION: SEQ ID NO: 37:

GCCCCCCTGA GATCAAGTNC GGGGAGUCAC UGUGCUUCGU GCAG               44

(2) INFORMATION FOR SEQ ID NO: 38:

(i) SEQUENCE CHARACTERISTICS:
        (A) LENGTH: 44 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: YES (vi) ORIGINAL SOURCE:
        (A) ORGANISM: Homo sapiens (xi) SEQUENCE DESCRIPTION: SEQ ID NO: 38:

CTGCACGAAG CACAGTGACT CCCCGCACUU GAUCUCAGGG GGGC               44

(2) INFORMATION FOR SEQ ID NO: 39:

(i) SEQUENCE CHARACTERISTICS:

(A) LENGTH: 44 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Homo sapiens (ix) FEATURE:
            (A) NAME/KEY: modified_base
            (B) LOCATION: 19
            (D) OTHER INFORMATION: /mod_base= i (ix) FEATURE:
            (A) NAME/KEY: misc_feature
            (B) LOCATION: 27
            (D) OTHER INFORMATION: N is a purine or a pyrimidine (ix) FEATURE:
            (A) NAME/KEY: misc_feature
            (B) LOCATION: 31
            (D) OTHER INFORMATION: N is a purine or a pyrimidine (ix) FEATURE:
            (A) NAME/KEY: misc_feature
            (B) LOCATION: 33
            (D) OTHER INFORMATION: N is a purine or a pyrimidine (ix) FEATURE:
            (A) NAME/KEY: misc_feature
            (B) LOCATION: 36..37
            (D) OTHER INFORMATION: N is a purine or a pyrimidine (ix) FEATURE:
            (A) NAME/KEY: misc_feature
            (B) LOCATION: 40
            (D) OTHER INFORMATION: N is a purine or a pyrimidine (xi) SEQUENCE DESCRIPTION: SEQ ID NO: 39:

GCCCCCCTGA GATCAAGTNC GGGGAGNCAC NGNGCNNCGN GCAG                                44

(2) INFORMATION FOR SEQ ID NO: 40:

(i) SEQUENCE CHARACTERISTICS:
            (A) LENGTH: 44 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: YES (vi) ORIGINAL SOURCE:
            (A) ORGANISM: Homo sapiens (ix) FEATURE:
            (A) NAME/KEY: misc_feature
            (B) LOCATION: 29..30
            (D) OTHER INFORMATION: N is a purine or a pyrimidine (ix) FEATURE:
            (A) NAME/KEY: misc_feature
            (B) LOCATION: 33
            (D) OTHER INFORMATION: N is a purine or a pyrimidine (ix) FEATURE:
            (A) NAME/KEY: misc_feature
            (B) LOCATION: 35
            (D) OTHER INFORMATION: N is a purine or a pyrimidine (xi) SEQUENCE DESCRIPTION: SEQ ID NO: 40:

CTGCACGAAG CACAGTGACT CCCCGCACNN GANCNCAGGG GGGC					44

(2) INFORMATION FOR SEQ ID NO: 41:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (ix) FEATURE:
        (A) NAME/KEY: modified_base
        (B) LOCATION: 19
        (D) OTHER INFORMATION: /mod_base= i (xi) SEQUENCE DESCRIPTION: SEQ ID NO: 41:

GCCCCCCTGA GATCAAGTNC GGGGAG					26

(2) INFORMATION FOR SEQ ID NO: 42:

(i) SEQUENCE CHARACTERISTICS:
        (A) LENGTH: 28 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: YES (vi) ORIGINAL SOURCE:
        (A) ORGANISM: Homo sapiens (xi) SEQUENCE DESCRIPTION: SEQ ID NO: 42:

CTGCACGAAG CACAGTGACT CCCCGCAC					28

(2) INFORMATION FOR SEQ ID NO: 43:

(i) SEQUENCE CHARACTERISTICS:
        (A) LENGTH: 44 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (ix) FEATURE:
        (A) NAME/KEY: modified_base
        (B) LOCATION: 19
        (D) OTHER INFORMATION: /mod_base= i (xi) SEQUENCE DESCRIPTION: SEQ ID NO: 43:

GCCCCCCTGA GATCAAGTNC AGGGAGUCAC UGUGCUUCGU GCAG					44

(2) INFORMATION FOR SEQ ID NO: 44:

(i) SEQUENCE CHARACTERISTICS:
        (A) LENGTH: 44 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: YES (vi) ORIGINAL SOURCE:
        (A) ORGANISM: Homo sapiens (xi) SEQUENCE DESCRIPTION: SEQ ID NO: 44:

CTGCACGAAG CACAGTGACT CCCUGCACUU GAUCUCAGGG GGGC              44

(2) INFORMATION FOR SEQ ID NO: 45:

(i) SEQUENCE CHARACTERISTICS:
        (A) LENGTH: 44 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (ix) FEATURE:
        (A) NAME/KEY: modified_base
        (B) LOCATION: 19
        (D) OTHER INFORMATION: /mod_base= i (ix) FEATURE:
        (A) NAME/KEY: misc_feature
        (B) LOCATION: 27
        (D) OTHER INFORMATION: N is a purine or a pyrimidine (ix) FEATURE:
        (A) NAME/KEY: misc_feature
        (B) LOCATION: 31
        (D) OTHER INFORMATION: N is a purine or a pyrimidine (ix) FEATURE:
        (A) NAME/KEY: misc_feature
        (B) LOCATION: 33
        (D) OTHER INFORMATION: N is a purine or a pyrimidine (ix) FEATURE:
        (A) NAME/KEY: misc_feature
        (B) LOCATION: 36..37
        (D) OTHER INFORMATION: N is a purine or a pyrimidine (ix) FEATURE:
        (A) NAME/KEY: misc_feature
        (B) LOCATION: 40
        (D) OTHER INFORMATION: N is a purine or a pyrimidine (xi) SEQUENCE DESCRIPTION: SEQ ID NO: 45:

GCCCCCCTGA GATCAAGTNC AGGGAGNCAC NGNGCNNCGN GCAG              44

(2) INFORMATION FOR SEQ ID NO: 46:

(i) SEQUENCE CHARACTERISTICS:
        (A) LENGTH: 44 base pairs (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: YES (vi) ORIGINAL SOURCE:
            (A) ORGANISM: Homo sapiens (ix) FEATURE:
            (A) NAME/KEY: misc_feature
            (B) LOCATION: 24
            (D) OTHER INFORMATION: N is a purine or a pyrimidine (ix) FEATURE:
            (A) NAME/KEY: misc_feature
            (B) LOCATION: 29..30
            (D) OTHER INFORMATION: N is a purine or a pyrimidine (ix) FEATURE:
            (A) NAME/KEY: misc_feature
            (B) LOCATION: 33
            (D) OTHER INFORMATION: N is a purine or
                a pyrimidine (ix) FEATURE:
            (A) NAME/KEY: misc_feature
            (B) LOCATION: 35
            (D) OTHER INFORMATION: N is a purine
                or a pyrimidine (xi) SEQUENCE DESCRIPTION: SEQ ID NO: 46:

CTGCACGAAG CACAGTGACT CCCNGCACNN GANCNCAGGG GGGC                            44

(2) INFORMATION FOR SEQ ID NO: 47:

(i) SEQUENCE CHARACTERISTICS:
            (A) LENGTH: 26 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Homo sapiens (ix) FEATURE:
            (A) NAME/KEY: modified_base
            (B) LOCATION: 19
            (D) OTHER INFORMATION: /mod_base= i (ix) FEATURE:
            (A) NAME/KEY: misc_feature
            (B) LOCATION: 26
            (D) OTHER INFORMATION: sequence is shown with and without
                3'-terminal deoxyribosephosphate (xi) SEQUENCE DESCRIPTION: SEQ ID NO: 47:

GCCCCCCTGA GATCAAGTNC AGGGAG                                               26

(2) INFORMATION FOR SEQ ID NO: 48:

(i) SEQUENCE CHARACTERISTICS:
            (A) LENGTH: 26 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (A) ORGANISM: Homo sapiens (ix) FEATURE:
             (A) NAME/KEY: modified_base
             (B) LOCATION: 19
             (D) OTHER INFORMATION: /mod_base= i (ix) FEATURE:
             (A) NAME/KEY: misc_feature
             (B) LOCATION: 26
             (D) OTHER INFORMATION: sequence is shown with and without
                  3'-terminal deoxyribosephosphate (xi) SEQUENCE DESCRIPTION: SEQ ID NO: 48:

GCCCCCCTGA GATCAAGTNC GGGGAG                                               26

(2) INFORMATION FOR SEQ ID NO: 49:

(i) SEQUENCE CHARACTERISTICS:
             (A) LENGTH: 28 base pairs
             (B) TYPE: nucleic acid
             (C) STRANDEDNESS: double
             (D) TOPOLOGY: linear (ii) MOLECULE TYPE: DNA (genomic)

(iii) HYPOTHETICAL: NO (iv) ANTI-SENSE: YES (vi) ORIGINAL SOURCE:
             (A) ORGANISM: Homo sapiens (ix) FEATURE:
             (A) NAME/KEY: misc_feature
             (B) LOCATION: 28
             (D) OTHER INFORMATION: sequence is shown with and without
                  3'-terminal deoxyribosephosphate (xi) SEQUENCE DESCRIPTION: SEQ ID NO: 49:

CTGCACGAAG CACAGTGACT CCCCGCAC                                             28

(2) INFORMATION FOR SEQ ID NO: 50:

(i) SEQUENCE CHARACTERISTICS:
             (A) LENGTH: 26 base pairs
             (B) TYPE: nucleic acid
             (C) STRANDEDNESS: double
             (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (A) ORGANISM: Homo sapiens (ix) FEATURE:
             (A) NAME/KEY: modified_base
             (B) LOCATION: 19
             (D) OTHER INFORMATION: /mod_base= i (ix) FEATURE:
             (A) NAME/KEY: misc_feature
             (B) LOCATION: 26
             (D) OTHER INFORMATION: sequence is shown with and without 3'-terminal deoxyribosephosphate (xi) SEQUENCE DESCRIPTION: SEQ ID NO: 50:

GCCCCCCTGA GATCAAGTNC AGGGAG                                          26

(2) INFORMATION FOR SEQ ID NO: 51:

(i) SEQUENCE CHARACTERISTICS:
        (A) LENGTH: 23 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: YES (vi) ORIGINAL SOURCE:
        (A) ORGANISM: Homo sapiens (ix) FEATURE:
        (A) NAME/KEY: misc_feature
        (B) LOCATION: 23
        (D) OTHER INFORMATION: sequence is shown with and without
            3'-terminal deoxyribosephosphate (xi) SEQUENCE DESCRIPTION: SEQ ID NO: 51:

CTGCACGAAG CACAGTGACT CCC                                             23

(2) INFORMATION FOR SEQ ID NO: 52:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (ix) FEATURE:
        (A) NAME/KEY: modified_base
        (B) LOCATION: 10
        (D) OTHER INFORMATION: /mod_base= i (ix) FEATURE:
        (A) NAME/KEY: modified_base
        (B) LOCATION: 12
        (D) OTHER INFORMATION: /mod_base= i (ix) FEATURE:
        (A) NAME/KEY: modified_base
        (B) LOCATION: 15..16
        (C) IDENTIFICATION METHOD: experimental
        (D) OTHER INFORMATION: /mod_base= i (ix) FEATURE:
        (A) NAME/KEY: modified_base
        (B) LOCATION: 19
        (D) OTHER INFORMATION: /mod_base= i (xi) SEQUENCE DESCRIPTION: SEQ ID NO: 52:

GCCCCCCTGN GNTCNNGTNC                                                 20

(2) INFORMATION FOR SEQ ID NO: 53:

```
     (i) SEQUENCE CHARACTERISTICS:
         (A) LENGTH: 41 base pairs
         (B) TYPE: nucleic acid
         (C) STRANDEDNESS: double
         (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: Homo sapiens (ix) FEATURE:
         (A) NAME/KEY: modified_base
         (B) LOCATION: 10
         (D) OTHER INFORMATION: /mod_base= i (ix) FEATURE:
         (A) NAME/KEY: modified_base
         (B) LOCATION: 12
         (D) OTHER INFORMATION: /mod_base= i (ix) FEATURE:
         (A) NAME/KEY: modified_base
         (B) LOCATION: 15..16
         (D) OTHER INFORMATION: /mod_base= i (ix) FEATURE:
         (A) NAME/KEY: modified_base
         (B) LOCATION: 19
         (D) OTHER INFORMATION: /mod_base= i (xi) SEQUENCE DESCRIPTION: SEQ ID NO: 53:

GCCCCCCTGN GNTCNNGTNC GGGGAGUCAC UGUGCUUCGU G                    41

(2) INFORMATION FOR SEQ ID NO: 54:

(i) SEQUENCE CHARACTERISTICS:
         (A) LENGTH: 41 base pairs
         (B) TYPE: nucleic acid
         (C) STRANDEDNESS: double
         (D) TOPOLOGY: linear (ii) MOLECULE TYPE: DNA (genomic)

(iii) HYPOTHETICAL: NO (iv) ANTI-SENSE: YES (vi) ORIGINAL SOURCE:
         (A) ORGANISM: Homo sapiens (xi) SEQUENCE DESCRIPTION: SEQ ID NO: 54:

CACGAAGCAC AGTGACTCCC CGCACCCGAC CCCAGGGGGG C                    41

(2) INFORMATION FOR SEQ ID NO: 55:

(i) SEQUENCE CHARACTERISTICS:
         (A) LENGTH: 41 base pairs
         (B) TYPE: nucleic acid
         (C) STRANDEDNESS: double
         (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: Homo sapiens (ix) FEATURE:
```

(A) NAME/KEY: modified_base
            (B) LOCATION: 10
            (D) OTHER INFORMATION: /mod_base= i (ix) FEATURE:
            (A) NAME/KEY: modified_base
            (B) LOCATION: 12
            (D) OTHER INFORMATION: /mod_base= i (ix) FEATURE:
            (A) NAME/KEY: modified_base
            (B) LOCATION: 15..16
            (D) OTHER INFORMATION: /mod_base= i (ix) FEATURE:
            (A) NAME/KEY: modified_base
            (B) LOCATION: 19
            (D) OTHER INFORMATION: /mod_base= i (xi) SEQUENCE DESCRIPTION: SEQ ID NO: 55:

GCCCCCCTGN GNTCNNGTNC AGGGAGUCAC UGUGCUUCGU G          41

(2) INFORMATION FOR SEQ ID NO: 56:

(i) SEQUENCE CHARACTERISTICS:
            (A) LENGTH: 41 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: YES (vi) ORIGINAL SOURCE:
            (A) ORGANISM: Homo sapiens (xi) SEQUENCE DESCRIPTION: SEQ ID NO: 56:

CACGAAGCAC AGTGACTCCC UGCACCCGAC CCCAGGGGGG C          41

(2) INFORMATION FOR SEQ ID NO: 57:

(i) SEQUENCE CHARACTERISTICS:
            (A) LENGTH: 20 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: YES (vi) ORIGINAL SOURCE:
            (A) ORGANISM: Homo sapiens (xi) SEQUENCE DESCRIPTION: SEQ ID NO: 57:

GCACCCGACC CCAGGGGGGC          20

(2) INFORMATION FOR SEQ ID NO: 58:

(i) SEQUENCE CHARACTERISTICS:
            (A) LENGTH: 24 base pairs
            (B) TYPE: nucleic acid
            (C) STRANDEDNESS: double
            (D) TOPOLOGY: circular (ii) MOLECULE TYPE: DNA (genomic)

(iii) HYPOTHETICAL: NO (iv) ANTI-SENSE: NO (vi) ORIGINAL SOURCE:
             (A) ORGANISM: Mycobacterium tuberculosis (xi) SEQUENCE DESCRIPTION: SEQ ID NO: 58:

CCAGCATCCT GACCTACCAC GTAG                                                  24

(2) INFORMATION FOR SEQ ID NO: 59:

(i) SEQUENCE CHARACTERISTICS:
            (A) LENGTH: 68 base pairs
            (B) TYPE: nucleic acid
            (C) STRANDEDNESS: double
            (D) TOPOLOGY: circular (ii) MOLECULE TYPE: DNA (genomic)

(iii) HYPOTHETICAL: NO (iv) ANTI-SENSE: NO (vi) ORIGINAL SOURCE:
             (A) ORGANISM: Mycobacterium tuberculosis (xi) SEQUENCE DESCRIPTION: SEQ ID NO: 59:

CCAGCATCCT GACCTACCAC GTAGTGGCCG GCCAAACCAG CCCGGCCAAC GTCGTCGGCA           60

CCCGTCAG                                                                    68

(2) INFORMATION FOR SEQ ID NO: 60:

(i) SEQUENCE CHARACTERISTICS:
            (A) LENGTH: 20 base pairs
            (B) TYPE: nucleic acid
            (C) STRANDEDNESS: double
            (D) TOPOLOGY: circular (ii) MOLECULE TYPE: DNA (genomic)

(iii) HYPOTHETICAL: NO (iv) ANTI-SENSE: YES (vi) ORIGINAL SOURCE:
             (A) ORGANISM: Mycobacterium tuberculosis (ix) FEATURE:
             (A) NAME/KEY: modified_base
             (B) LOCATION: 4
             (D) OTHER INFORMATION: /mod_base= i (ix) FEATURE:
             (A) NAME/KEY: modified_base
             (B) LOCATION: 14
             (D) OTHER INFORMATION: /mod_base= i (ix) FEATURE:
             (A) NAME/KEY: modified_base
             (B) LOCATION: 17
             (D) OTHER INFORMATION: /mod_base= i (xi) SEQUENCE DESCRIPTION: SEQ ID NO: 60:

CTGNCGGGTG CCGNCGNCGT                                                       20

(2) INFORMATION FOR SEQ ID NO: 61:

(i) SEQUENCE CHARACTERISTICS:
            (A) LENGTH: 76 base pairs
            (B) TYPE: nucleic acid
            (C) STRANDEDNESS: double
            (D) TOPOLOGY: circular (ii) MOLECULE TYPE: DNA (genomic)

(iii) HYPOTHETICAL: NO (iv) ANTI-SENSE: NO (vi) ORIGINAL SOURCE:
                (A) ORGANISM: Mycobacterium tuberculosis (xi) SEQUENCE DESCRIPTION: SEQ ID NO: 61:

CCAGCATCCT GACCTACCAC GTAGUGGCCG GCCAAACCAG CCCGGCCAAC GCCGCCGGCA      60

CCCGCCAGCC CCCCCC      76

(2) INFORMATION FOR SEQ ID NO: 62:

(i) SEQUENCE CHARACTERISTICS:
            (A) LENGTH: 76 base pairs
            (B) TYPE: nucleic acid
            (C) STRANDEDNESS: double
            (D) TOPOLOGY: circular (ii) MOLECULE TYPE: DNA (genomic)

(iii) HYPOTHETICAL: NO (iv) ANTI-SENSE: YES (vi) ORIGINAL SOURCE:
            (A) ORGANISM: Mycobacterium tuberculosis (ix) FEATURE:
            (A) NAME/KEY: modified_base
            (B) LOCATION: 12
            (D) OTHER INFORMATION: /mod_base= i (ix) FEATURE:
            (A) NAME/KEY: modified_base
            (B) LOCATION: 22
            (D) OTHER INFORMATION: /mod_base= i (ix) FEATURE:
            (A) NAME/KEY: modified_base
            (B) LOCATION: 25
            (D) OTHER INFORMATION: /mod_base= i (xi) SEQUENCE DESCRIPTION: SEQ ID NO: 62:

GGGGGGGGCT GNCGGGTGCC GNCGNCGTTG GCCGGGCTGG TTTGGCCGGC CACUACGUGG      60

UAGGUCAGGA UGCUGG      76

(2) INFORMATION FOR SEQ ID NO: 63:

(i) SEQUENCE CHARACTERISTICS:
            (A) LENGTH: 51 base pairs
            (B) TYPE: nucleic acid
            (C) STRANDEDNESS: double
            (D) TOPOLOGY: circular (ii) MOLECULE TYPE: DNA (genomic)

(iii) HYPOTHETICAL: NO (iv) ANTI-SENSE: NO (vi) ORIGINAL SOURCE:
            (A) ORGANISM: Mycobacterium tuberculosis (xi) SEQUENCE DESCRIPTION: SEQ ID NO: 63:

GGCCGGCCAA ACCAGCCCGG CCAACGCCGC CGGCACCCGC CAGCCCCCCC C      51

(2) INFORMATION FOR SEQ ID NO: 64:

(i) SEQUENCE CHARACTERISTICS:
            (A) LENGTH: 25 base pairs (B) TYPE: nucleic acid
(C) STRANDEDNESS: double
(D) TOPOLOGY: circular (ii) MOLECULE TYPE: DNA (genomic)

(iii) HYPOTHETICAL: NO (iv) ANTI-SENSE: NO (vi) ORIGINAL SOURCE:
(A) ORGANISM: Mycobacterium tuberculosis (xi) SEQUENCE DESCRIPTION: SEQ ID NO: 64:

CCAGCATCCT GACCTACCAC GTAGT 25

(2) INFORMATION FOR SEQ ID NO: 65:

(i) SEQUENCE CHARACTERISTICS:
(A) LENGTH: 76 base pairs
(B) TYPE: nucleic acid
(C) STRANDEDNESS: double
(D) TOPOLOGY: circular (ii) MOLECULE TYPE: DNA (genomic)

(iii) HYPOTHETICAL: NO (iv) ANTI-SENSE: NO (vi) ORIGINAL SOURCE:
(A) ORGANISM: Mycobacterium tuberculosis (xi) SEQUENCE DESCRIPTION: SEQ ID NO: 65:

CCAGCATCCT GACCTACCAC GTAGTGGCCG GCCAAACCAG CCCGGCCAAC GCCGCCGGCA 60

CCCGCCAGCC CCCCCC 76

(2) INFORMATION FOR SEQ ID NO: 66:

(i) SEQUENCE CHARACTERISTICS:
(A) LENGTH: 76 base pairs
(B) TYPE: nucleic acid
(C) STRANDEDNESS: double
(D) TOPOLOGY: circular (ii) MOLECULE TYPE: DNA (genomic)

(iii) HYPOTHETICAL: NO (iv) ANTI-SENSE: YES (vi) ORIGINAL SOURCE:
(A) ORGANISM: Mycobacterium tuberculosis (ix) FEATURE:
(A) NAME/KEY: modified_base
(B) LOCATION: 12
(D) OTHER INFORMATION: /mod_base= i (ix) FEATURE:
(A) NAME/KEY: modified_base
(B) LOCATION: 22
(D) OTHER INFORMATION: /mod_base= i (ix) FEATURE:
(A) NAME/KEY: modified_base
(B) LOCATION: 25
(D) OTHER INFORMATION: /mod_base= i (xi) SEQUENCE DESCRIPTION: SEQ ID NO: 66:

GGGGGGGGCT GNCGGGTGCC GNCGNCGTTG GCCGGGCTGG TTTGGCCGGC CACUACGUGG 60

UAGGUCAGGA UGCUGG 76

(2) INFORMATION FOR SEQ ID NO: 67:

(i) SEQUENCE CHARACTERISTICS:
        (A) LENGTH: 116 base pairs
        (B) TYPE: nucleic acid
        (C) STRANDEDNESS: double
        (D) TOPOLOGY: circular (ii) MOLECULE TYPE: DNA (genomic)

(iii) HYPOTHETICAL: NO (iv) ANTI-SENSE: NO (vi) ORIGINAL SOURCE:
        (A) ORGANISM: Mycobacterium tuberculosis (xi) SEQUENCE DESCRIPTION: SEQ ID NO: 67:

```
GGCCTCGGTG CAGGGAATGT CGCAGGACCC GGUCGCGGTG GCGGCCTCGA ACAATCCGGA      60

GTTGACAACG CTGACGGCTG CACTGTCGGG CCAGCTCAAT CCGCAAGTAA ACCTGG         116
```

(2) INFORMATION FOR SEQ ID NO: 68:

(i) SEQUENCE CHARACTERISTICS:
        (A) LENGTH: 130 base pairs
        (B) TYPE: nucleic acid
        (C) STRANDEDNESS: double
        (D) TOPOLOGY: circular (ii) MOLECULE TYPE: DNA (genomic)

(iii) HYPOTHETICAL: NO (iv) ANTI-SENSE: NO (vi) ORIGINAL SOURCE:
        (A) ORGANISM: Mycobacterium tuberculosis (xi) SEQUENCE DESCRIPTION: SEQ ID NO: 68:

```
CATCCTGACC TACCACGTAG TGGCCGGCCA AACCAGCCCG GCCAACGTCG TCGGCACCCG      60

TCAGACCCTC CAGGGCGCCA GCGTGACGGT GACCGGTCAG GGTAACAGCC TCAAGGTCGG     120

TAACGCCGAC                                                            130
```

(2) INFORMATION FOR SEQ ID NO: 69:

(i) SEQUENCE CHARACTERISTICS:
        (A) LENGTH: 408 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO: 69:

```
ACTTCCTGCG CTTTGCTGTC TTCGTCAACG GCGAGAGCGT GGAGGAGAAC GCCAATGTGG      60

TGGTGCGGCT GCTCATCCGG AAGCCTGAGT GCTTCGGACC CGCCCTGCGG GGTGAGGGTG    120

GCTCAGGGCT GCTGGCTGCC ATCGAAGAGG CCATCCGCAT CTCCGAGGAC CCTGCGAGGG    180

ATGGCCCAGG CATCCGCAGG GACCGGCGGC GCGAGCACTT TGGTGAGGAA CCGCCTGAAG    240

AAAACCGGGT GCACCTGGGA CACGCCATCA TGTCCTTCTA TGCCGCCTTG ATCGACCTGC    300
```

```
TCGGACACTG TGCACCAGAG ATGCATCTAA TCCAAGCCGG CAAGGGTGAG GCCCTGCGGA       360

TCCGCGCCAT CCTCCACTCC CTTGTGCCCT TGGAGGACCT TGTGGGCA                    408
```